(12) United States Patent
Fahey et al.

(10) Patent No.: US 12,357,792 B2
(45) Date of Patent: Jul. 15, 2025

(54) INTERNAL RECHARGING SYSTEMS AND METHODS OF USE

(71) Applicant: Shifamed Holdings, LLC, Campbell, CA (US)

(72) Inventors: Brian J. Fahey, Menlo Park, CA (US); Amr Salahieh, Saratoga, CA (US); Marwan Berrada, Los Gatos, CA (US); Tom Saul, Moss Beach, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 605 days.

(21) Appl. No.: 17/419,454

(22) PCT Filed: Jan. 2, 2020

(86) PCT No.: PCT/US2020/012059
§ 371 (c)(1),
(2) Date: Jun. 29, 2021

(87) PCT Pub. No.: WO2020/142613
PCT Pub. Date: Jul. 9, 2020

(65) Prior Publication Data
US 2022/0118228 A1    Apr. 21, 2022

Related U.S. Application Data

(60) Provisional application No. 62/788,642, filed on Jan. 4, 2019.

(51) Int. Cl.
*A61M 25/04* (2006.01)
*A61B 5/00* (2006.01)
(Continued)

(52) U.S. Cl.
CPC .......... *A61M 25/04* (2013.01); *A61B 5/0031* (2013.01); *A61B 5/0215* (2013.01);
(Continued)

(58) Field of Classification Search
CPC .......... A61M 25/04; A61M 2025/1097; A61B 5/0031; A61B 5/0215; A61B 5/6853; A61B 2560/0219; G16H 40/63
See application file for complete search history.

(56) References Cited

U.S. PATENT DOCUMENTS

| | | |
|---|---|---|
| 3,874,388 A | 4/1975 | King et al. |
| 4,601,309 A | 7/1986 | Chang |

(Continued)

FOREIGN PATENT DOCUMENTS

| | | |
|---|---|---|
| AU | 2005211243 | 8/2005 |
| AU | 2010344182 | 8/2012 |

(Continued)

OTHER PUBLICATIONS

Extended European Search Report received for Application No. 20896031.0, Applicant: Shifamed Holdings, LLC; Date of Mailing: Dec. 7, 2023; 11 pages.

(Continued)

*Primary Examiner* — Joel Lamprecht
*Assistant Examiner* — Amy Shafqat
(74) *Attorney, Agent, or Firm* — Perkins Coie LLP

(57) ABSTRACT

Implant device recharging methods, devices, and systems. The implantable devices that are recharged can include one or more sensors. The implantable devices can include one or more receive transducers. A recharging catheter can emit energy to the one or more receive transducers to recharge an implantable device power source.

12 Claims, 3 Drawing Sheets

(51) Int. Cl.
*A61B 5/0215* (2006.01)
*A61M 25/10* (2013.01)
(52) U.S. Cl.
CPC .... *A61B 5/6853* (2013.01); *A61B 2560/0219* (2013.01); *A61M 2025/1097* (2013.01)

(56) References Cited

U.S. PATENT DOCUMENTS

| | | | |
|---|---|---|---|
| 4,662,355 A | 5/1987 | Pieronne et al. | |
| 4,705,507 A | 11/1987 | Boyles | |
| 4,836,204 A | 6/1989 | Landymore et al. | |
| 4,979,955 A | 12/1990 | Smith | |
| 4,995,857 A | 2/1991 | Arnold | |
| 5,186,431 A | 2/1993 | Tamari | |
| 5,267,940 A | 12/1993 | Moulder | |
| 5,290,227 A | 3/1994 | Pasque | |
| 5,312,341 A | 5/1994 | Turi | |
| 5,326,374 A | 7/1994 | Ilbawi et al. | |
| 5,332,402 A | 7/1994 | Teitelbaum | |
| 5,334,217 A | 8/1994 | Das | |
| 5,409,019 A | 4/1995 | Wilk | |
| 5,429,144 A | 7/1995 | Wilk | |
| 5,500,015 A | 3/1996 | Deac | |
| 5,531,759 A | 7/1996 | Kensey et al. | |
| 5,545,137 A | 8/1996 | Rudie et al. | |
| 5,556,386 A | 9/1996 | Todd | |
| 5,584,803 A | 12/1996 | Stevens et al. | |
| 5,597,377 A | 1/1997 | Aldea | |
| 5,645,559 A | 7/1997 | Hachtman et al. | |
| 5,655,548 A | 8/1997 | Nelson et al. | |
| 5,662,711 A | 9/1997 | Douglas | |
| 5,702,412 A | 12/1997 | Popov et al. | |
| 5,725,552 A | 3/1998 | Kotula et al. | |
| 5,741,297 A | 4/1998 | Simon | |
| 5,795,307 A | 8/1998 | Krueger | |
| 5,810,836 A | 9/1998 | Hussein et al. | |
| 5,814,089 A | 9/1998 | Stokes et al. | |
| 5,824,071 A | 10/1998 | Nelson et al. | |
| 5,916,193 A | 6/1999 | Stevens et al. | |
| 5,941,850 A | 8/1999 | Shah et al. | |
| 5,944,019 A | 8/1999 | Kundson et al. | |
| 5,948,006 A | 9/1999 | Mann | |
| 5,949,632 A | 9/1999 | Barreras et al. | |
| 5,957,949 A | 9/1999 | Leonhardt et al. | |
| 6,039,759 A | 3/2000 | Carpentier et al. | |
| 6,066,163 A | 5/2000 | John | |
| 6,067,474 A | 5/2000 | Schulman et al. | |
| 6,077,298 A | 6/2000 | Tu et al. | |
| 6,099,495 A | 8/2000 | Kinghorn et al. | |
| 6,120,534 A | 9/2000 | Ruiz | |
| 6,126,686 A | 10/2000 | Badylak et al. | |
| 6,165,188 A | 12/2000 | Saadat et al. | |
| 6,165,209 A | 12/2000 | Patterson et al. | |
| 6,166,518 A | 12/2000 | Echarri et al. | |
| 6,210,318 B1 | 4/2001 | Lederman | |
| 6,217,541 B1 | 4/2001 | Yu | |
| 6,240,316 B1 | 5/2001 | Richmond et al. | |
| 6,240,322 B1 | 5/2001 | Peterfeso et al. | |
| 6,242,762 B1 | 6/2001 | Brown et al. | |
| 6,254,564 B1 | 7/2001 | Wilk et al. | |
| 6,259,951 B1 | 7/2001 | Kuzma et al. | |
| 6,260,552 B1 | 7/2001 | Mortier et al. | |
| 6,270,526 B1 | 8/2001 | Cox | |
| 6,277,078 B1 | 8/2001 | Porat et al. | |
| 6,302,892 B1 | 10/2001 | Wilk | |
| 6,328,699 B1 | 12/2001 | Eigler et al. | |
| 6,344,022 B1 | 2/2002 | Jarvik | |
| 6,354,991 B1 | 3/2002 | Gross et al. | |
| 6,358,277 B1 | 3/2002 | Duran | |
| 6,381,496 B1 | 4/2002 | Meadows et al. | |
| 6,406,422 B1 | 6/2002 | Landesberg | |
| 6,447,539 B1 | 9/2002 | Nelson et al. | |
| 6,451,051 B2 | 9/2002 | Drasler et al. | |
| 6,458,153 B1 | 10/2002 | Bailey et al. | |
| 6,468,303 B1 | 10/2002 | Amplatz et al. | |
| 6,478,776 B1 | 11/2002 | Rosenman et al. | |
| 6,491,705 B1 | 12/2002 | Gifford, III et al. | |
| 6,516,227 B1 | 2/2003 | Meadows et al. | |
| 6,527,698 B1 | 3/2003 | Kung et al. | |
| 6,544,208 B2 | 4/2003 | Ethier et al. | |
| 6,562,066 B1 | 5/2003 | Martin | |
| 6,572,652 B2 | 6/2003 | Shaknovich | |
| 6,589,198 B1 | 7/2003 | Soltanpour et al. | |
| 6,622,048 B1 | 9/2003 | Mann et al. | |
| 6,632,169 B2 | 10/2003 | Korakianitis et al. | |
| 6,638,303 B1 | 10/2003 | Campbell | |
| 6,641,610 B2 | 11/2003 | Wolf et al. | |
| 6,650,943 B1 | 11/2003 | Whitehurst et al. | |
| 6,652,578 B2 | 11/2003 | Bailey et al. | |
| 6,685,664 B2 | 2/2004 | Levin et al. | |
| 6,712,836 B1 | 3/2004 | Berg et al. | |
| 6,733,485 B1 | 5/2004 | Whitehurst et al. | |
| 6,735,474 B1 | 5/2004 | Loeb et al. | |
| 6,735,475 B1 | 5/2004 | Kuzma et al. | |
| 6,782,292 B2 | 8/2004 | Whitehurst | |
| 6,783,499 B2 | 8/2004 | Schwartz | |
| 6,788,975 B1 | 9/2004 | Whitehurst et al. | |
| 6,820,019 B1 | 11/2004 | Kelly et al. | |
| 6,832,114 B1 | 12/2004 | Whitehurst et al. | |
| 6,845,267 B2 | 1/2005 | Harrison et al. | |
| 6,862,479 B1 | 3/2005 | Whitehurst et al. | |
| 6,871,099 B1 | 3/2005 | Kuzma et al. | |
| 6,885,895 B1 | 4/2005 | Whitehurst et al. | |
| 6,909,920 B2 | 6/2005 | Lokhoff et al. | |
| 6,911,043 B2 | 6/2005 | Myers et al. | |
| 6,922,590 B1 | 7/2005 | Whitehurst | |
| 6,926,670 B2 | 8/2005 | Rich et al. | |
| 6,937,891 B2 | 8/2005 | Rodriguez et al. | |
| 6,950,706 B2 | 9/2005 | Jensen et al. | |
| 6,950,707 B2 | 9/2005 | Whitehurst | |
| 6,970,741 B1 | 11/2005 | Whitehurst et al. | |
| 7,001,409 B2 | 2/2006 | Amplatz | |
| 7,003,352 B1 | 2/2006 | Whitehurst | |
| 7,011,095 B2 | 3/2006 | Wolf et al. | |
| 7,013,177 B1 | 3/2006 | Meadows et al. | |
| 7,024,246 B2 | 4/2006 | Acosta et al. | |
| 7,054,689 B1 | 5/2006 | Whitehurst et al. | |
| 7,054,691 B1 | 5/2006 | Kuzma et al. | |
| 7,056,294 B2 | 6/2006 | Khairkhahan et al. | |
| 7,070,577 B1 | 7/2006 | Haller et al. | |
| 7,089,057 B2 | 8/2006 | Heathershaw et al. | |
| 7,110,821 B1 | 9/2006 | Ross | |
| 7,136,701 B2 | 11/2006 | Greatbatch et al. | |
| 7,146,209 B2 | 12/2006 | Gross et al. | |
| 7,149,587 B2 | 12/2006 | Wardle et al. | |
| 7,149,773 B2 | 12/2006 | Haller et al. | |
| 7,151,961 B1 | 12/2006 | Mcclure et al. | |
| 7,155,279 B2 | 12/2006 | Whitehurst et al. | |
| 7,155,284 B1 | 12/2006 | Whitehurst et al. | |
| 7,167,751 B1 | 1/2007 | Whitehurst et al. | |
| 7,175,656 B2 | 2/2007 | Khairkhahan | |
| 7,177,698 B2 | 2/2007 | Klosterman et al. | |
| 7,203,548 B2 | 4/2007 | Bradley et al. | |
| 7,254,449 B2 | 8/2007 | Karunasiri | |
| 7,270,675 B2 | 9/2007 | Chun et al. | |
| 7,292,890 B2 | 11/2007 | Bradley et al. | |
| 7,294,115 B1 | 11/2007 | Wilk | |
| 7,308,303 B2 | 12/2007 | Whitehurst et al. | |
| 7,311,690 B2 | 12/2007 | Burnett | |
| 7,311,730 B2 | 12/2007 | Gabbay | |
| 7,317,947 B2 | 1/2008 | Wahlstrand et al. | |
| 7,317,951 B2 | 1/2008 | Schneider et al. | |
| 7,330,756 B2 | 2/2008 | Marnfeldt | |
| 7,337,003 B2 | 2/2008 | Malinowski | |
| 7,349,741 B2 | 3/2008 | Maltan et al. | |
| 7,389,134 B1 | 6/2008 | Karicherla et al. | |
| 7,390,310 B2 | 6/2008 | McCusker et al. | |
| 7,433,737 B2 | 10/2008 | He et al. | |
| 7,437,193 B2 | 10/2008 | Parramon et al. | |
| 7,444,180 B2 | 10/2008 | Kuzma et al. | |
| 7,481,759 B2 | 1/2009 | Whitehurst et al. | |
| 7,483,746 B2 | 1/2009 | Lee et al. | |
| 7,483,748 B2 | 1/2009 | Torgerson et al. | |
| 7,498,516 B1 | 3/2009 | He | |

(56) References Cited

U.S. PATENT DOCUMENTS

| | | |
|---|---|---|
| 7,513,908 B2 | 4/2009 | Lattouf |
| 7,524,329 B2 | 4/2009 | Rucker |
| 7,524,330 B2 | 4/2009 | Berreklouw |
| 7,524,332 B2 | 4/2009 | Osborne et al. |
| 7,532,936 B2 | 5/2009 | Erickson et al. |
| 7,608,067 B2 | 10/2009 | Bonni |
| 7,610,100 B2 | 10/2009 | Jaax et al. |
| 7,617,001 B2 | 11/2009 | Penner et al. |
| 7,634,318 B2 | 12/2009 | Tran et al. |
| 7,672,732 B2 | 3/2010 | Sun et al. |
| 7,684,867 B2 | 3/2010 | Whitehurst et al. |
| 7,699,059 B2 | 4/2010 | Fonseca et al. |
| 7,706,892 B2 | 4/2010 | Haller et al. |
| 7,729,758 B2 | 6/2010 | Parramon et al. |
| 7,736,327 B2 | 6/2010 | Wilk et al. |
| 7,742,817 B2 | 6/2010 | Malinowski et al. |
| 7,761,165 B1 | 7/2010 | Haller et al. |
| 7,769,467 B1 | 8/2010 | Emadi et al. |
| 7,777,641 B2 | 8/2010 | Karunasiri et al. |
| 7,780,725 B2 | 8/2010 | Haug et al. |
| 7,783,359 B2 | 8/2010 | Meadows |
| 7,794,473 B2 | 9/2010 | Tessmer et al. |
| 7,801,602 B2 | 9/2010 | Mcclure et al. |
| 7,803,021 B1 | 9/2010 | Brase |
| 7,805,200 B2 | 9/2010 | Kast et al. |
| 7,805,202 B2 | 9/2010 | Kuzma et al. |
| 7,806,921 B2 | 10/2010 | Hoffman |
| 7,813,804 B1 | 10/2010 | Jaax |
| 7,818,060 B2 | 10/2010 | Torgerson |
| 7,835,803 B1 | 11/2010 | Malinowski et al. |
| 7,840,268 B2 | 11/2010 | Blischak et al. |
| 7,840,279 B2 | 11/2010 | He |
| 7,853,321 B2 | 12/2010 | Whitehurst et al. |
| 7,857,819 B2 | 12/2010 | Jaax et al. |
| 7,860,570 B2 | 12/2010 | Whitehurst et al. |
| 7,860,579 B2 | 12/2010 | Goetzinger et al. |
| 7,877,136 B1 | 1/2011 | Moffitt et al. |
| 7,892,246 B2 | 2/2011 | Akin et al. |
| 7,905,901 B2 | 3/2011 | Corcoran et al. |
| 7,922,764 B2 | 4/2011 | Gordy et al. |
| 7,938,840 B2 | 5/2011 | Golden et al. |
| 7,941,227 B2 | 5/2011 | Barker |
| 7,945,323 B2 | 5/2011 | Jaax et al. |
| 7,957,805 B2 | 6/2011 | He |
| 7,967,769 B2 | 6/2011 | Faul et al. |
| 7,974,706 B2 | 7/2011 | Moffitt et al. |
| 7,988,724 B2 | 8/2011 | Salahieh et al. |
| 7,991,483 B1 | 8/2011 | Atanasoska et al. |
| 8,012,198 B2 | 9/2011 | Hill et al. |
| 8,016,877 B2 | 9/2011 | Seguin et al. |
| 8,019,443 B2 | 9/2011 | Schleicher et al. |
| 8,027,735 B1 | 9/2011 | Tziviskos et al. |
| 8,043,360 B2 | 10/2011 | McNamara et al. |
| 8,046,073 B1 | 10/2011 | Pianca |
| 8,060,209 B2 | 11/2011 | Digiore et al. |
| 8,070,708 B2 | 12/2011 | Rottenberg et al. |
| 8,086,307 B2 | 12/2011 | Virag et al. |
| 8,091,556 B2 | 1/2012 | Keren et al. |
| 8,096,959 B2 | 1/2012 | Stewart et al. |
| 8,099,168 B2 | 1/2012 | Roche |
| 8,145,314 B2 | 3/2012 | Mcdonald |
| 8,147,545 B2 | 4/2012 | Avior |
| 8,157,860 B2 | 4/2012 | McNamara et al. |
| 8,172,896 B2 | 5/2012 | McNamara et al. |
| 8,175,710 B2 | 5/2012 | He |
| 8,175,717 B2 | 5/2012 | Haller et al. |
| 8,192,418 B2 | 6/2012 | Robinson et al. |
| 8,209,017 B1 | 6/2012 | Mcdonald |
| 8,219,196 B2 | 7/2012 | Torgerson |
| 8,235,916 B2 | 8/2012 | Whiting et al. |
| 8,235,933 B2 | 8/2012 | Keren et al. |
| 8,244,377 B1 | 8/2012 | Pianca et al. |
| 8,246,677 B2 | 8/2012 | Ryan |
| 8,252,042 B2 | 8/2012 | McNamara et al. |
| 8,260,412 B2 | 9/2012 | Krause et al. |
| 8,260,432 B2 | 9/2012 | Digiore et al. |
| 8,260,434 B2 | 9/2012 | Digiore et al. |
| 8,265,771 B2 | 9/2012 | Donofrio et al. |
| 8,271,089 B2 | 9/2012 | Dinsmoor et al. |
| 8,271,094 B1 | 9/2012 | Moffitt et al. |
| 8,280,500 B2 | 10/2012 | Chow |
| 8,290,599 B2 | 10/2012 | Walter et al. |
| 8,303,511 B2 | 11/2012 | Eigler et al. |
| 8,328,751 B2 | 12/2012 | Keren et al. |
| 8,332,049 B2 | 12/2012 | Pianca et al. |
| 8,335,570 B2 | 12/2012 | Mcdonald |
| 8,340,782 B2 | 12/2012 | Mcdonald et al. |
| 8,348,996 B2 | 1/2013 | Tuval et al. |
| 8,352,035 B2 | 1/2013 | Schleicher et al. |
| 8,352,039 B2 | 1/2013 | Davis et al. |
| 8,359,107 B2 | 1/2013 | Pianca et al. |
| 8,364,279 B2 | 1/2013 | Mcdonald et al. |
| 8,374,686 B2 | 2/2013 | Ghanem et al. |
| 8,380,324 B2 | 2/2013 | Mcdonald et al. |
| 8,380,325 B2 | 2/2013 | Mcdonald |
| 8,386,038 B2 | 2/2013 | Bianchi et al. |
| 8,398,708 B2 | 3/2013 | Meiri et al. |
| 8,401,214 B2 | 3/2013 | Perkins et al. |
| 8,401,654 B1 | 3/2013 | Foster et al. |
| 8,406,893 B2 | 3/2013 | Krause et al. |
| 8,406,897 B2 | 3/2013 | Mcdonald et al. |
| 8,412,332 B2 | 4/2013 | Massoud-Ansari et al. |
| 8,412,349 B2 | 4/2013 | Barker |
| 8,417,343 B2 | 4/2013 | Bolea et al. |
| 8,433,409 B2 | 4/2013 | Johnson et al. |
| 8,437,851 B2 | 5/2013 | Corbucci et al. |
| 8,442,649 B2 | 5/2013 | Mcdonald |
| 8,452,407 B2 | 5/2013 | Whitehurst et al. |
| 8,460,366 B2 | 6/2013 | Rowe |
| 8,460,372 B2 | 6/2013 | McNamara et al. |
| 8,478,423 B2 | 7/2013 | Mcdonald et al. |
| 8,494,654 B2 | 7/2013 | Pianca et al. |
| 8,506,514 B2 | 8/2013 | Pedersen et al. |
| 8,515,541 B1 | 8/2013 | Jaax et al. |
| 8,527,045 B2 | 9/2013 | Krause et al. |
| 8,531,153 B2 | 9/2013 | Baarman et al. |
| 8,538,538 B2 | 9/2013 | Torgerson et al. |
| 8,543,210 B2 | 9/2013 | Sharma |
| 8,548,582 B2 | 10/2013 | Mcdonald et al. |
| 8,597,225 B2 | 12/2013 | Kapadia |
| 8,600,507 B2 | 12/2013 | Brase et al. |
| 8,600,512 B2 | 12/2013 | Whitehurst et al. |
| 8,600,518 B2 | 12/2013 | Meadows et al. |
| 8,606,355 B1 | 12/2013 | Krause |
| 8,626,297 B2 | 1/2014 | Jaax et al. |
| 8,638,062 B2 | 1/2014 | Baarman et al. |
| 8,647,381 B2 | 2/2014 | Essinger et al. |
| 8,655,451 B2 | 2/2014 | Klosterman et al. |
| 8,670,823 B2 | 3/2014 | Murtonen |
| 8,676,322 B2 | 3/2014 | Whitehurst et al. |
| 8,682,439 B2 | 3/2014 | Derohan et al. |
| 8,688,235 B1 | 4/2014 | Pianca et al. |
| 8,696,611 B2 | 4/2014 | Nitzan et al. |
| 8,712,542 B2 | 4/2014 | Mcmorrow et al. |
| 8,718,790 B2 | 5/2014 | Pianca |
| 8,740,962 B2 | 6/2014 | Finch et al. |
| 8,744,568 B2 | 6/2014 | Weber |
| 8,744,591 B2 | 6/2014 | Davis et al. |
| 8,745,845 B2 | 6/2014 | Finch et al. |
| 8,747,458 B2 | 6/2014 | Tuval et al. |
| 8,752,258 B2 | 6/2014 | Finch et al. |
| 8,755,881 B2 | 6/2014 | Kaiser et al. |
| 8,761,886 B2 | 6/2014 | Stancer et al. |
| 8,764,848 B2 | 7/2014 | Callaghan et al. |
| 8,768,488 B2 | 7/2014 | Barker |
| 8,774,941 B2 | 7/2014 | Pianca |
| 8,792,994 B2 | 7/2014 | Venancio |
| 8,805,537 B1 | 8/2014 | Cong et al. |
| 8,812,107 B2 | 8/2014 | Virag et al. |
| 8,818,483 B2 | 8/2014 | Romero |
| 8,818,505 B2 | 8/2014 | Bhunia et al. |
| 8,818,508 B2 | 8/2014 | Scheiner |
| 8,845,705 B2 | 9/2014 | Perkins et al. |
| 8,849,396 B2 | 9/2014 | Derohan et al. |

(56) References Cited

U.S. PATENT DOCUMENTS

| | | |
|---|---|---|
| 8,849,414 B2 | 9/2014 | Lee |
| 8,849,419 B2 | 9/2014 | Lee |
| 8,849,422 B2 | 9/2014 | Pianca |
| 8,868,207 B2 | 10/2014 | Mcdonald et al. |
| 8,874,206 B2 | 10/2014 | Malinowski et al. |
| 8,882,697 B2 | 11/2014 | Celermajer et al. |
| 8,897,876 B2 | 11/2014 | Sundaramurthy et al. |
| 8,909,352 B2 | 12/2014 | Venook et al. |
| 8,909,354 B2 | 12/2014 | Orinski |
| 8,914,112 B2 | 12/2014 | Whitehurst et al. |
| 8,923,970 B2 | 12/2014 | Bar-yoseph et al. |
| 8,936,630 B2 | 1/2015 | Denison et al. |
| 8,942,935 B2 | 1/2015 | Michaels et al. |
| 8,951,223 B2 | 2/2015 | McNamara et al. |
| 8,965,511 B2 | 2/2015 | Greiner et al. |
| 8,965,528 B2 | 2/2015 | Howard |
| 8,979,758 B2 | 3/2015 | Stein et al. |
| 9,005,155 B2 | 4/2015 | Sugimoto |
| 9,008,778 B2 | 4/2015 | Gupta et al. |
| 9,020,589 B2 | 4/2015 | Torgerson |
| 9,034,034 B2 | 5/2015 | Nitzan et al. |
| 9,056,206 B2 | 6/2015 | Torgerson et al. |
| 9,065,284 B2 | 6/2015 | Malpas et al. |
| 9,072,447 B2 | 7/2015 | Chow |
| 9,079,039 B2 | 7/2015 | Carlson et al. |
| 9,095,701 B2 | 8/2015 | Govea et al. |
| 9,101,755 B2 | 8/2015 | Pianca |
| 9,119,967 B2 | 9/2015 | Gupta et al. |
| 9,119,970 B2 | 9/2015 | Va |
| 9,132,276 B2 | 9/2015 | Meskens |
| 9,138,213 B2 | 9/2015 | Amin et al. |
| 9,143,003 B2 | 9/2015 | Baarman et al. |
| 9,162,048 B2 | 10/2015 | Romero et al. |
| 9,162,055 B2 | 10/2015 | Pianca et al. |
| 9,180,291 B2 | 11/2015 | Leven |
| 9,180,303 B2 | 11/2015 | Goetz |
| 9,192,772 B1 | 11/2015 | Tsukamoto et al. |
| 9,204,842 B2 | 12/2015 | Mothilal et al. |
| 9,205,236 B2 | 12/2015 | McNamara et al. |
| 9,205,251 B2 | 12/2015 | Govea et al. |
| 9,215,075 B1 | 12/2015 | Poltorak |
| 9,216,282 B1 | 12/2015 | Moffitt et al. |
| 9,216,563 B2 | 12/2015 | Barner |
| 9,232,997 B2 | 1/2016 | Sugimoto et al. |
| 9,259,571 B2 | 2/2016 | Straka et al. |
| 9,265,934 B2 | 2/2016 | Pianca et al. |
| 9,277,995 B2 | 3/2016 | Celermajer et al. |
| 9,283,378 B2 | 3/2016 | Govea |
| 9,289,592 B2 | 3/2016 | Chinn et al. |
| 9,289,600 B2 | 3/2016 | Govea et al. |
| 9,302,094 B2 | 4/2016 | Govea |
| 9,302,113 B2 | 4/2016 | Ranu et al. |
| 9,320,891 B2 | 4/2016 | Anderson et al. |
| 9,320,901 B2 | 4/2016 | Torgerson et al. |
| 9,339,657 B2 | 5/2016 | Stancer et al. |
| 9,345,897 B2 | 5/2016 | Dorman et al. |
| 9,352,145 B2 | 5/2016 | Whitehurst et al. |
| 9,358,371 B2 | 6/2016 | McNamara et al. |
| 9,364,658 B2 | 6/2016 | Wechter |
| 9,381,342 B2 | 7/2016 | Barker |
| 9,393,422 B2 | 7/2016 | Moffitt et al. |
| 9,399,131 B2 | 7/2016 | Digiore et al. |
| 9,402,993 B2 | 8/2016 | Howard et al. |
| 9,403,011 B2 | 8/2016 | Mercanzini |
| 9,409,032 B2 | 8/2016 | Brase et al. |
| 9,415,154 B2 | 8/2016 | Leven |
| 9,415,212 B2 | 8/2016 | Barker |
| 9,415,213 B2 | 8/2016 | Venook et al. |
| 9,440,066 B2 | 9/2016 | Black |
| 9,456,812 B2 | 10/2016 | Finch et al. |
| 9,492,655 B2 | 11/2016 | Pianca et al. |
| 9,498,635 B2 | 11/2016 | Dellamano et al. |
| 9,498,636 B2 | 11/2016 | Dellamano et al. |
| 9,504,839 B2 | 11/2016 | Leven |
| 9,504,842 B2 | 11/2016 | Guardiani et al. |
| 9,517,334 B2 | 12/2016 | Barner et al. |
| 9,533,141 B2 | 1/2017 | Black et al. |
| 9,537,344 B2 | 1/2017 | Thompson et al. |
| 9,539,432 B2 | 1/2017 | Dellamano et al. |
| 9,544,068 B2 | 1/2017 | Arbabian et al. |
| 9,560,980 B2 | 2/2017 | Charlton et al. |
| 9,561,362 B2 | 2/2017 | Malinowski |
| 9,597,505 B2 | 3/2017 | Donofrio et al. |
| 9,604,048 B2 | 3/2017 | Govea |
| 9,604,050 B2 | 3/2017 | Barker |
| 9,604,066 B2 | 3/2017 | Carbunaru et al. |
| 9,604,068 B2 | 3/2017 | Malinowski |
| 9,610,041 B2 | 4/2017 | Foster et al. |
| 9,610,434 B2 | 4/2017 | Barker |
| 9,629,658 B2 | 4/2017 | Barker |
| 9,629,715 B2 | 4/2017 | Nitzan et al. |
| 9,642,993 B2 | 5/2017 | McNamara et al. |
| 9,643,010 B2 | 5/2017 | Ranu |
| 9,647,462 B2 | 5/2017 | Angst et al. |
| 9,649,480 B2 | 5/2017 | Sugimoto et al. |
| 9,649,489 B2 | 5/2017 | Wechter et al. |
| 9,655,528 B2 | 5/2017 | Zhu |
| 9,656,093 B2 | 5/2017 | Villarta et al. |
| 9,662,506 B2 | 5/2017 | Govea |
| 9,669,210 B2 | 6/2017 | Barker et al. |
| 9,681,948 B2 | 6/2017 | Levi et al. |
| 9,700,350 B2 | 7/2017 | Barker |
| 9,707,382 B2 | 7/2017 | Nitzan et al. |
| 9,707,406 B1 | 7/2017 | Dellamano et al. |
| 9,713,696 B2 | 7/2017 | Yacoby et al. |
| 9,713,725 B2 | 7/2017 | Bobgan et al. |
| 9,724,499 B2 | 8/2017 | Rottenberg et al. |
| 9,744,368 B2 | 8/2017 | Dinsmoor |
| 9,757,107 B2 | 9/2017 | McNamara et al. |
| 9,770,598 B2 | 9/2017 | Malinowski et al. |
| 9,775,636 B2 | 10/2017 | Fazio et al. |
| 9,775,987 B2 | 10/2017 | Donofrio et al. |
| 9,782,581 B2 | 10/2017 | Howard et al. |
| 9,782,582 B2 | 10/2017 | Govea et al. |
| 9,782,597 B2 | 10/2017 | Shanahan et al. |
| 9,808,613 B2 | 11/2017 | Mcdonald et al. |
| 9,814,881 B2 | 11/2017 | Moffitt |
| 9,826,963 B2 | 11/2017 | Scott et al. |
| 9,833,611 B2 | 12/2017 | Govea et al. |
| 9,833,615 B2 | 12/2017 | Pereira et al. |
| 9,833,622 B2 | 12/2017 | Moffitt et al. |
| 9,833,629 B2 | 12/2017 | Dellamano et al. |
| 9,839,788 B2 | 12/2017 | Dellamano et al. |
| 9,849,025 B2 | 12/2017 | Zaveri et al. |
| 9,867,981 B2 | 1/2018 | Black et al. |
| 9,878,148 B2 | 1/2018 | Leven et al. |
| 9,883,836 B2 | 2/2018 | Cahan et al. |
| 9,889,304 B2 | 2/2018 | Mercanzini |
| 9,889,308 B2 | 2/2018 | Dellamano et al. |
| 9,901,737 B2 | 2/2018 | Moffitt et al. |
| 9,907,972 B2 | 3/2018 | Kameli |
| 9,918,856 B2 | 3/2018 | Favier et al. |
| 9,919,148 B2 | 3/2018 | Howard et al. |
| 9,925,377 B2 | 3/2018 | Moffitt et al. |
| 9,925,378 B2 | 3/2018 | Moffitt et al. |
| 9,931,109 B2 | 4/2018 | Burckhardt et al. |
| 9,937,036 B2 | 4/2018 | Sugimoto et al. |
| 9,943,670 B2 | 4/2018 | Keren et al. |
| 9,956,000 B2 | 5/2018 | Gardanier et al. |
| 9,956,394 B2 | 5/2018 | Howard et al. |
| 9,974,959 B2 | 5/2018 | Moffitt et al. |
| 9,980,815 B2 | 5/2018 | Nitzan et al. |
| 9,986,989 B2 | 6/2018 | Roche et al. |
| 9,987,482 B2 | 6/2018 | Nageri et al. |
| 9,987,493 B2 | 6/2018 | Torgerson et al. |
| 9,993,168 B2 | 6/2018 | Huang et al. |
| 10,022,054 B2 | 7/2018 | Najafi et al. |
| 10,022,542 B2 | 7/2018 | Yip et al. |
| 10,022,549 B2 | 7/2018 | Dellamano et al. |
| 10,027,179 B1 | 7/2018 | Bello et al. |
| 10,035,013 B2 | 7/2018 | Desalles et al. |
| 10,045,766 B2 | 8/2018 | McNamara et al. |
| 10,058,696 B2 | 8/2018 | Stouffer |
| 10,075,026 B2 | 9/2018 | Badr et al. |

(56) References Cited

U.S. PATENT DOCUMENTS

| | | |
|---|---|---|
| 10,076,403 B1 | 9/2018 | Eigler et al. |
| 10,076,408 B2 | 9/2018 | Basinger et al. |
| 10,117,580 B1 | 11/2018 | Puryear et al. |
| 10,117,740 B1 | 11/2018 | Lee |
| 10,130,806 B2 | 11/2018 | Leven et al. |
| 10,137,304 B2 | 11/2018 | Kallmyer |
| 10,147,248 B2 | 12/2018 | Graafstra |
| 10,173,055 B2 | 1/2019 | Howard et al. |
| 10,176,933 B2 | 1/2019 | Irazoqui et al. |
| 10,179,234 B2 | 1/2019 | Leven |
| 10,179,237 B2 | 1/2019 | Kane et al. |
| 10,188,375 B2 | 1/2019 | McNamara et al. |
| 10,201,686 B2 | 2/2019 | Saul et al. |
| 10,204,706 B2 | 2/2019 | Davis et al. |
| 10,207,087 B2 | 2/2019 | Keren |
| 10,226,616 B2 | 3/2019 | Barker |
| 10,232,169 B2 | 3/2019 | Govea et al. |
| 10,251,676 B2 | 4/2019 | Brunner et al. |
| 10,251,740 B2 | 4/2019 | Eigler et al. |
| 10,286,205 B2 | 5/2019 | Steinke et al. |
| 10,286,215 B2 | 5/2019 | Perkins et al. |
| 10,292,690 B2 | 5/2019 | Celermajer et al. |
| 10,307,602 B2 | 6/2019 | Leven |
| 10,335,607 B2 | 7/2019 | Orinski |
| 10,342,983 B2 | 7/2019 | Nageri et al. |
| 10,357,357 B2 | 7/2019 | Levi et al. |
| 10,368,981 B2 | 8/2019 | Nitzan et al. |
| 10,376,359 B2 | 8/2019 | Essinger et al. |
| 10,376,680 B2 | 8/2019 | McNamara et al. |
| 10,391,319 B2 | 8/2019 | Shuros et al. |
| 10,398,421 B2 | 9/2019 | Celermajer |
| 10,398,899 B2 | 9/2019 | Torgerson |
| 10,405,903 B1 | 9/2019 | Biesinger et al. |
| 10,413,284 B2 | 9/2019 | McNamara et al. |
| 10,413,286 B2 | 9/2019 | McNamara et al. |
| 10,413,737 B2 | 9/2019 | Bokil et al. |
| 10,413,739 B2 | 9/2019 | Funderburk |
| 10,426,968 B2 | 10/2019 | Casse et al. |
| 10,449,382 B2 | 10/2019 | Casse et al. |
| 10,463,305 B2 | 11/2019 | An et al. |
| 10,463,477 B2 | 11/2019 | Forcucci et al. |
| 10,463,490 B2 | 11/2019 | Rottenberg et al. |
| 10,471,251 B1 | 11/2019 | Manicka |
| 10,478,594 B2 | 11/2019 | Yacoby et al. |
| 10,512,784 B2 | 12/2019 | Hahn et al. |
| 10,554,069 B2 | 2/2020 | Paralikar et al. |
| 10,568,751 B2 | 2/2020 | McNamara |
| 10,576,267 B2 | 3/2020 | Reddy et al. |
| 10,576,269 B2 | 3/2020 | Steinke et al. |
| 10,583,247 B2 | 3/2020 | Mandro |
| 10,588,611 B2 | 3/2020 | Magnin et al. |
| 10,603,485 B2 | 3/2020 | Nageri |
| 10,603,499 B2 | 3/2020 | Lopez |
| 10,603,505 B2 | 3/2020 | Casse et al. |
| 10,610,210 B2 | 4/2020 | Finch et al. |
| 10,610,694 B2 | 4/2020 | Reinke et al. |
| 10,624,621 B2 | 4/2020 | Celermajer |
| 10,625,072 B2 | 4/2020 | Serran |
| 10,632,292 B2 | 4/2020 | Forcucci et al. |
| 10,638,955 B2 | 5/2020 | Rowland et al. |
| 10,639,459 B2 | 5/2020 | Nitzan et al. |
| 10,639,486 B2 | 5/2020 | Linder et al. |
| 10,655,024 B2 | 5/2020 | Yadavalli et al. |
| 10,667,896 B2 | 6/2020 | Delaney, Jr. et al. |
| 10,667,904 B2 | 6/2020 | Marquez et al. |
| 10,668,294 B2 | 6/2020 | Koop et al. |
| 10,675,450 B2 | 6/2020 | Finch |
| 10,675,476 B2 | 6/2020 | Reddy et al. |
| 10,695,571 B2 | 6/2020 | Dellamano et al. |
| 10,709,886 B2 | 7/2020 | Nagaoka et al. |
| 10,709,888 B2 | 7/2020 | Pianca |
| 10,716,935 B2 | 7/2020 | Leven et al. |
| 10,751,542 B2 | 8/2020 | Demmer et al. |
| 10,772,557 B2 | 9/2020 | Windolf |
| 10,780,278 B2 | 9/2020 | Hahn et al. |
| 10,806,352 B2 | 10/2020 | Sweeney et al. |
| 10,813,744 B2 | 10/2020 | Gupta et al. |
| 10,820,987 B2 | 11/2020 | Basinger et al. |
| 10,821,286 B2 | 11/2020 | Acklin et al. |
| 10,828,151 B2 | 11/2020 | Nitzan et al. |
| 10,835,394 B2 | 11/2020 | Nae et al. |
| 10,835,757 B2 | 11/2020 | Register et al. |
| 10,849,522 B2 | 12/2020 | Eddy et al. |
| 10,856,767 B2 | 12/2020 | Dettmann et al. |
| 10,870,008 B2 | 12/2020 | Hahn et al. |
| 10,881,863 B2 | 1/2021 | Maile et al. |
| 10,881,869 B2 | 1/2021 | Maile et al. |
| 10,894,163 B2 | 1/2021 | Stahmann |
| 10,898,698 B1 | 1/2021 | Eigler et al. |
| 10,898,719 B2 | 1/2021 | Pivonka et al. |
| 10,910,863 B2 | 2/2021 | Otten |
| 10,912,645 B2 | 2/2021 | Rottenberg et al. |
| 10,918,476 B2 | 2/2021 | Otts |
| 10,918,873 B2 | 2/2021 | Funderburk |
| 10,918,875 B2 | 2/2021 | Maile et al. |
| 10,925,706 B2 | 2/2021 | Eigler et al. |
| 10,932,786 B2 | 3/2021 | McNamara et al. |
| 10,933,234 B2 | 3/2021 | Molnar et al. |
| 10,940,296 B2 | 3/2021 | Keren |
| 10,960,214 B2 | 3/2021 | Steinke et al. |
| 10,967,192 B2 | 4/2021 | Lui et al. |
| 10,973,425 B2 | 4/2021 | Cao |
| 11,002,990 B2 | 5/2021 | Lee et al. |
| 11,020,592 B2 | 6/2021 | Tyulmankov et al. |
| 11,020,595 B2 | 6/2021 | Koop |
| 11,045,658 B2 | 6/2021 | Iyer et al. |
| 11,050,263 B2 | 6/2021 | Bae et al. |
| 11,052,259 B2 | 7/2021 | Stinauer et al. |
| 11,056,267 B2 | 7/2021 | Iyer et al. |
| 11,090,491 B2 | 8/2021 | Mishra et al. |
| 11,097,096 B2 | 8/2021 | Linden et al. |
| 11,116,988 B2 | 9/2021 | Maile et al. |
| 11,135,439 B2 | 10/2021 | Deshazo et al. |
| 11,147,979 B2 | 10/2021 | Linder et al. |
| 11,160,980 B2 | 11/2021 | Mishra et al. |
| 11,160,984 B2 | 11/2021 | Deshazo et al. |
| 11,167,128 B2 | 11/2021 | Villarta |
| 11,172,959 B2 | 11/2021 | Leven |
| 11,198,006 B1 | 12/2021 | Nijlunsing et al. |
| 11,207,532 B2 | 12/2021 | Eddy et al. |
| 11,224,743 B2 | 1/2022 | Govea et al. |
| 11,241,166 B1 | 2/2022 | Lee |
| 11,241,576 B2 | 2/2022 | Hansen et al. |
| 11,253,685 B2 | 2/2022 | Fahey et al. |
| 11,291,846 B2 | 4/2022 | Chiang |
| 11,311,373 B2 | 4/2022 | Gutierrez et al. |
| 11,331,493 B2 | 5/2022 | Pivonka et al. |
| 11,344,728 B2 | 5/2022 | Mercanzini et al. |
| 11,357,992 B2 | 6/2022 | Nageri et al. |
| 11,357,995 B2 | 6/2022 | Dellamano et al. |
| 11,364,109 B2 | 6/2022 | Basinger et al. |
| 11,369,267 B2 | 6/2022 | Melodia et al. |
| 11,383,083 B2 | 7/2022 | Bolea |
| 11,389,583 B2 | 7/2022 | Noshadi |
| 11,400,291 B2 | 8/2022 | Gnansia et al. |
| 11,426,595 B2 | 8/2022 | Leven et al. |
| 11,458,309 B2 | 10/2022 | Zorman et al. |
| 11,467,665 B2 | 10/2022 | Gribetz |
| 11,493,556 B2 | 11/2022 | Deshazo |
| 11,497,914 B2 | 11/2022 | Hahn et al. |
| 11,504,526 B2 | 11/2022 | Zhu |
| 11,511,121 B2 | 11/2022 | Sit et al. |
| 11,524,174 B2 | 12/2022 | Vansickle et al. |
| 11,529,510 B2 | 12/2022 | Leven |
| 11,565,131 B2 | 1/2023 | Vansickle et al. |
| 11,577,075 B1 | 2/2023 | Gaudiani |
| 11,583,387 B2 | 2/2023 | Boysset et al. |
| 11,607,163 B2 | 3/2023 | Iyer et al. |
| 11,622,695 B1 | 4/2023 | Andriola et al. |
| 11,623,095 B2 | 4/2023 | Esteller et al. |
| 11,633,194 B2 | 4/2023 | Alexander et al. |
| 11,642,065 B2 | 5/2023 | Felix et al. |
| 11,679,263 B2 | 6/2023 | Hsu et al. |
| 11,696,681 B2 | 7/2023 | Felix et al. |

(56) References Cited

U.S. PATENT DOCUMENTS

| | | |
|---|---|---|
| 11,697,019 B2 | 7/2023 | Mazanec |
| 11,701,019 B2 | 7/2023 | Gunn et al. |
| 11,717,695 B2 | 8/2023 | Keil |
| 11,737,667 B2 | 8/2023 | Fink et al. |
| 11,737,896 B2 | 8/2023 | Bhamra et al. |
| 11,745,023 B2 | 9/2023 | Keil et al. |
| 11,791,657 B2 | 10/2023 | Rotfogel et al. |
| 11,801,369 B2 | 10/2023 | Fahey et al. |
| 11,806,547 B2 | 11/2023 | Howard |
| 2002/0072656 A1 | 6/2002 | Vantassel et al. |
| 2002/0151770 A1 | 10/2002 | Noll et al. |
| 2002/0169371 A1 | 11/2002 | Gilderdale |
| 2002/0169475 A1 | 11/2002 | Gainor et al. |
| 2002/0177891 A1 | 11/2002 | Miles et al. |
| 2003/0125798 A1 | 7/2003 | Martin |
| 2003/0127090 A1 | 7/2003 | Gifford et al. |
| 2003/0163190 A1 | 8/2003 | LaFont et al. |
| 2003/0204222 A1 | 10/2003 | Leinders et al. |
| 2003/0208244 A1 | 11/2003 | Stein et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0106954 A1 | 6/2004 | Whitehurst et al. |
| 2004/0122477 A1 | 6/2004 | Whitehurst et al. |
| 2004/0143294 A1 | 7/2004 | Corcoran et al. |
| 2004/0147869 A1 | 7/2004 | Wolf et al. |
| 2004/0158143 A1* | 8/2004 | Flaherty ............ A61B 17/12109 600/407 |
| 2004/0162514 A1 | 8/2004 | Alferness et al. |
| 2004/0162590 A1 | 8/2004 | Mcclure et al. |
| 2004/0186566 A1 | 9/2004 | Hindrichs et al. |
| 2004/0210190 A1 | 10/2004 | Kohler et al. |
| 2004/0215067 A1 | 10/2004 | Stiger et al. |
| 2004/0215323 A1 | 10/2004 | Stiger |
| 2005/0004641 A1 | 1/2005 | Pappu |
| 2005/0027332 A1 | 2/2005 | Avrahami et al. |
| 2005/0033351 A1 | 2/2005 | Newton |
| 2005/0134452 A1 | 6/2005 | Smith |
| 2005/0148925 A1 | 7/2005 | Rottenberg et al. |
| 2005/0159789 A1 | 7/2005 | Brockway et al. |
| 2005/0165344 A1 | 7/2005 | Dobak, III |
| 2005/0192627 A1 | 9/2005 | Whisenant et al. |
| 2005/0204811 A1 | 9/2005 | Neff |
| 2005/0288722 A1 | 12/2005 | Eigler et al. |
| 2006/0009810 A1 | 1/2006 | Mann et al. |
| 2006/0025857 A1 | 2/2006 | Bergheim et al. |
| 2006/0047205 A1 | 3/2006 | Ludomirsky et al. |
| 2006/0064135 A1 | 3/2006 | Brockway |
| 2006/0111660 A1 | 5/2006 | Wolf et al. |
| 2006/0167522 A1 | 7/2006 | Malinowski |
| 2006/0200030 A1 | 9/2006 | White et al. |
| 2006/0241717 A1 | 10/2006 | Mcgivern et al. |
| 2007/0010837 A1 | 1/2007 | Tanaka |
| 2007/0010852 A1 | 1/2007 | Blaeser et al. |
| 2007/0043435 A1 | 2/2007 | Seguin et al. |
| 2007/0050030 A1 | 3/2007 | Kim |
| 2007/0088220 A1 | 4/2007 | Stahmann |
| 2007/0142872 A1 | 6/2007 | Hackworth et al. |
| 2007/0150019 A1 | 6/2007 | Youker et al. |
| 2007/0213813 A1 | 9/2007 | Von Segesser et al. |
| 2007/0282157 A1 | 12/2007 | Rottenberg et al. |
| 2007/0293904 A1 | 12/2007 | Gelbart et al. |
| 2008/0027513 A1 | 1/2008 | Carbunaru |
| 2008/0033527 A1 | 2/2008 | Nunez et al. |
| 2008/0077184 A1 | 3/2008 | Denker et al. |
| 2008/0097276 A1 | 4/2008 | Bertrand et al. |
| 2008/0108904 A1 | 5/2008 | Heil |
| 2008/0119891 A1 | 5/2008 | Miles et al. |
| 2008/0171941 A1 | 7/2008 | Huelskamp et al. |
| 2008/0208083 A1 | 8/2008 | Lin et al. |
| 2008/0212261 A1 | 9/2008 | Ajayan et al. |
| 2008/0262566 A1 | 10/2008 | Jaax |
| 2008/0288019 A1 | 11/2008 | Heller |
| 2009/0005756 A1 | 1/2009 | Foster |
| 2009/0025459 A1 | 1/2009 | Zhang et al. |
| 2009/0036975 A1 | 2/2009 | Ward et al. |
| 2009/0105782 A1 | 4/2009 | Mickle et al. |
| 2009/0118779 A1 | 5/2009 | Najafi et al. |
| 2009/0132009 A1 | 5/2009 | Torgerson |
| 2009/0243956 A1 | 10/2009 | Keilman et al. |
| 2009/0248122 A1 | 10/2009 | Pianca |
| 2009/0248124 A1 | 10/2009 | Chinn et al. |
| 2009/0270742 A1 | 10/2009 | Wolinsky et al. |
| 2009/0275996 A1 | 11/2009 | Burnes et al. |
| 2009/0276040 A1 | 11/2009 | Rowe et al. |
| 2009/0281597 A1 | 11/2009 | Parramon et al. |
| 2010/0010565 A1 | 1/2010 | Gelbart et al. |
| 2010/0023103 A1 | 1/2010 | Elborno |
| 2010/0063375 A1 | 3/2010 | Kassab et al. |
| 2010/0076366 A1 | 3/2010 | Henderson, Sr. et al. |
| 2010/0076517 A1 | 3/2010 | Imran |
| 2010/0076535 A1 | 3/2010 | Pianca et al. |
| 2010/0106028 A1* | 4/2010 | Penner ................ A61B 5/0215 607/61 |
| 2010/0114195 A1 | 5/2010 | Burnes et al. |
| 2010/0114235 A1 | 5/2010 | Jiang et al. |
| 2010/0114244 A1 | 5/2010 | Manda et al. |
| 2010/0168672 A1 | 7/2010 | Carr |
| 2010/0179449 A1 | 7/2010 | Chow et al. |
| 2010/0198308 A1 | 8/2010 | Zhou et al. |
| 2010/0241195 A1 | 9/2010 | Meadows et al. |
| 2010/0249560 A1 | 9/2010 | Levinson et al. |
| 2010/0256696 A1 | 10/2010 | Schleicher et al. |
| 2010/0262021 A1 | 10/2010 | Yadav et al. |
| 2010/0262036 A1 | 10/2010 | Najafi et al. |
| 2010/0280568 A1 | 11/2010 | Bulkes et al. |
| 2010/0298930 A1 | 11/2010 | Orlov |
| 2010/0331918 A1 | 12/2010 | Digiore et al. |
| 2010/0331919 A1 | 12/2010 | Baldwin et al. |
| 2011/0009736 A1 | 1/2011 | Maltz et al. |
| 2011/0009933 A1 | 1/2011 | Barker |
| 2011/0034970 A1 | 2/2011 | Barker |
| 2011/0054515 A1 | 3/2011 | Bridgeman et al. |
| 2011/0082377 A1 | 4/2011 | Mahajan et al. |
| 2011/0093042 A1 | 4/2011 | Torgerson et al. |
| 2011/0106220 A1 | 5/2011 | Degiorgio et al. |
| 2011/0218480 A1 | 9/2011 | Rottenberg et al. |
| 2011/0218481 A1 | 9/2011 | Rottenberg et al. |
| 2011/0218549 A1 | 9/2011 | Barker |
| 2011/0224681 A1 | 9/2011 | Mcdonald |
| 2011/0230893 A1 | 9/2011 | Barker |
| 2011/0257723 A1 | 10/2011 | McNamara |
| 2011/0264194 A1 | 10/2011 | Griswold |
| 2011/0295183 A1 | 12/2011 | Finch et al. |
| 2011/0301479 A1 | 12/2011 | Ghanem et al. |
| 2012/0041287 A1 | 2/2012 | Goodall et al. |
| 2012/0046710 A1 | 2/2012 | Digiore et al. |
| 2012/0059431 A1 | 3/2012 | Williams et al. |
| 2012/0078320 A1 | 3/2012 | Schotzko et al. |
| 2012/0109243 A1 | 5/2012 | Hettrick et al. |
| 2012/0109261 A1 | 5/2012 | Stancer et al. |
| 2012/0123496 A1 | 5/2012 | Schotzko et al. |
| 2012/0191153 A1 | 7/2012 | Swerdlow et al. |
| 2012/0215295 A1 | 8/2012 | Pianca |
| 2012/0229272 A1 | 9/2012 | Jacob et al. |
| 2012/0235502 A1 | 9/2012 | Kesler et al. |
| 2012/0253261 A1 | 10/2012 | Poletto et al. |
| 2012/0265296 A1 | 10/2012 | McNamara et al. |
| 2012/0283773 A1 | 11/2012 | Van Tassel et al. |
| 2012/0290062 A1 | 11/2012 | McNamara et al. |
| 2012/0316610 A1 | 12/2012 | Pianca et al. |
| 2013/0085350 A1 | 4/2013 | Schugt et al. |
| 2013/0123569 A1 | 5/2013 | Gross |
| 2013/0144379 A1 | 6/2013 | Najafi et al. |
| 2013/0178783 A1 | 7/2013 | McNamara et al. |
| 2013/0178784 A1 | 7/2013 | McNamara et al. |
| 2013/0190799 A1 | 7/2013 | Clark |
| 2013/0192611 A1 | 8/2013 | Taepke, II et al. |
| 2013/0197336 A1 | 8/2013 | Flo et al. |
| 2013/0197423 A1 | 8/2013 | Keren et al. |
| 2013/0226266 A1 | 8/2013 | Murtonen et al. |
| 2013/0253343 A1 | 9/2013 | Waldhauser et al. |
| 2013/0282091 A1 | 10/2013 | Leven |

(56) References Cited

U.S. PATENT DOCUMENTS

| | | |
|---|---|---|
| 2013/0293025 A1 | 11/2013 | Xu et al. |
| 2013/0317587 A1 | 11/2013 | Barker |
| 2014/0012342 A1 | 1/2014 | Penner et al. |
| 2014/0018885 A1 | 1/2014 | Pianca |
| 2014/0028109 A1 | 1/2014 | Simon et al. |
| 2014/0039586 A1 | 2/2014 | Barker et al. |
| 2014/0046427 A1 | 2/2014 | Michalak |
| 2014/0081154 A1 | 3/2014 | Toth |
| 2014/0128795 A1 | 5/2014 | Karen et al. |
| 2014/0128796 A1 | 5/2014 | Keren et al. |
| 2014/0135647 A1 | 5/2014 | Wolf, II |
| 2014/0163449 A1 | 6/2014 | Rottenberg et al. |
| 2014/0172057 A1 | 6/2014 | Orinski |
| 2014/0180371 A1 | 6/2014 | Leven |
| 2014/0213915 A1 | 7/2014 | Doan et al. |
| 2014/0213959 A1 | 7/2014 | Nitzan et al. |
| 2014/0222040 A1 | 8/2014 | Park et al. |
| 2014/0277054 A1 | 9/2014 | McNamara et al. |
| 2014/0306807 A1 | 10/2014 | Rowland et al. |
| 2014/0324138 A1 | 10/2014 | Wentz et al. |
| 2014/0330256 A1 | 11/2014 | Hyde et al. |
| 2014/0343645 A1 | 11/2014 | Wechter |
| 2014/0343646 A1 | 11/2014 | Leven |
| 2015/0005856 A1 | 1/2015 | Pianca et al. |
| 2015/0005860 A1 | 1/2015 | Howard et al. |
| 2015/0018913 A1 | 1/2015 | Leven |
| 2015/0018917 A1 | 1/2015 | Wechter et al. |
| 2015/0034217 A1 | 2/2015 | Vad |
| 2015/0045865 A1 | 2/2015 | Nageri et al. |
| 2015/0051677 A1 | 2/2015 | Marnfeldt |
| 2015/0051681 A1 | 2/2015 | Hershey |
| 2015/0084585 A1 | 3/2015 | Moran |
| 2015/0119796 A1 | 4/2015 | Finch |
| 2015/0148731 A1 | 5/2015 | Mcnamara et al. |
| 2015/0157268 A1 | 6/2015 | Winshtein et al. |
| 2015/0200562 A1 | 7/2015 | Kilinc et al. |
| 2015/0208929 A1 | 7/2015 | Rowland et al. |
| 2015/0223707 A1 | 8/2015 | Ludoph |
| 2015/0230843 A1 | 8/2015 | Palmer et al. |
| 2015/0231387 A1 | 8/2015 | Harding et al. |
| 2015/0287544 A1 | 10/2015 | Irazoqui et al. |
| 2015/0360037 A1 | 12/2015 | Hahn et al. |
| 2015/0360049 A1 | 12/2015 | Kaplitt et al. |
| 2015/0374978 A1 | 12/2015 | Howard et al. |
| 2016/0022423 A1 | 1/2016 | Mcnamara et al. |
| 2016/0022995 A1 | 1/2016 | Kothandaraman et al. |
| 2016/0023008 A1 | 1/2016 | Kothandaraman |
| 2016/0051828 A1 | 2/2016 | Stahler et al. |
| 2016/0082247 A1 | 3/2016 | Black et al. |
| 2016/0089079 A1 | 3/2016 | Stein |
| 2016/0151179 A1 | 6/2016 | Favier et al. |
| 2016/0158561 A1 | 6/2016 | Reddy |
| 2016/0220357 A1 | 8/2016 | Anand et al. |
| 2016/0235999 A1 | 8/2016 | Nuta et al. |
| 2016/0256693 A1 | 9/2016 | Parramon |
| 2016/0303301 A1 | 10/2016 | Bluvshtein et al. |
| 2016/0375237 A1 | 12/2016 | Hahn et al. |
| 2017/0014067 A1 | 1/2017 | Peppou et al. |
| 2017/0043077 A1 | 2/2017 | Tuseth et al. |
| 2017/0105635 A1 | 4/2017 | Cho et al. |
| 2017/0113026 A1 | 4/2017 | Finch |
| 2017/0143978 A1 | 5/2017 | Barker |
| 2017/0259078 A1 | 9/2017 | Howard |
| 2017/0281936 A1 | 10/2017 | Aghassian et al. |
| 2017/0312078 A1 | 11/2017 | Krivoruchko |
| 2017/0326369 A1 | 11/2017 | Koop et al. |
| 2017/0326375 A1 | 11/2017 | Mcdonald et al. |
| 2017/0340460 A1 | 11/2017 | Rosen et al. |
| 2018/0014828 A1 | 1/2018 | Fonte et al. |
| 2018/0021569 A1 | 1/2018 | Pianca |
| 2018/0078773 A1 | 3/2018 | Thakur et al. |
| 2018/0117341 A1 | 5/2018 | Kane et al. |
| 2018/0168463 A1 | 6/2018 | Morris et al. |
| 2018/0250014 A1 | 9/2018 | Melanson et al. |
| 2018/0256865 A1 | 9/2018 | Finch et al. |
| 2018/0262037 A1 | 9/2018 | Meskeus |
| 2018/0369596 A1 | 12/2018 | Funderburk |
| 2018/0369606 A1 | 12/2018 | Zhang et al. |
| 2019/0000327 A1 | 1/2019 | Doan et al. |
| 2019/0015103 A1 | 1/2019 | Sharma |
| 2019/0019632 A1 | 1/2019 | Rusling et al. |
| 2019/0021861 A1 | 1/2019 | Finch |
| 2019/0038895 A1 | 2/2019 | Pianca et al. |
| 2019/0070421 A1 | 3/2019 | Chen |
| 2019/0104936 A1 | 4/2019 | Gunn et al. |
| 2019/0105503 A1 | 4/2019 | Leven |
| 2019/0167197 A1 | 6/2019 | Abuuassar et al. |
| 2019/0173505 A1 | 6/2019 | Koyama |
| 2019/0192864 A1 | 6/2019 | Koop et al. |
| 2019/0201695 A1 | 7/2019 | Hsu et al. |
| 2019/0209834 A1 | 7/2019 | Zhang et al. |
| 2019/0254814 A1 | 8/2019 | Nitzan et al. |
| 2019/0262118 A1 | 8/2019 | Eigler et al. |
| 2019/0269392 A1 | 9/2019 | Celermajer et al. |
| 2019/0269876 A1 | 9/2019 | Hsu et al. |
| 2019/0290924 A1 | 9/2019 | Funderburk |
| 2019/0307459 A1 | 10/2019 | Celermajer et al. |
| 2019/0328513 A1 | 10/2019 | Levi et al. |
| 2019/0336135 A1 | 11/2019 | Inouye et al. |
| 2019/0336163 A1 | 11/2019 | McNamara et al. |
| 2019/0343480 A1 | 11/2019 | Shute et al. |
| 2019/0350519 A1 | 11/2019 | Bailey et al. |
| 2020/0008870 A1 | 1/2020 | Gruba et al. |
| 2020/0009374 A1 | 1/2020 | Howard et al. |
| 2020/0023189 A1 | 1/2020 | Gribetz et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0188143 A1 | 6/2020 | McNamara |
| 2020/0196867 A1 | 6/2020 | Andersen et al. |
| 2020/0197178 A1 | 6/2020 | Vecchio |
| 2020/0229977 A1 | 7/2020 | Mixter et al. |
| 2020/0229981 A1 | 7/2020 | Mixter et al. |
| 2020/0229982 A1 | 7/2020 | Mixter et al. |
| 2020/0245991 A1 | 8/2020 | Celermajer |
| 2020/0253615 A1 | 8/2020 | Melanson et al. |
| 2020/0260991 A1 | 8/2020 | Rowlaud et al. |
| 2020/0261705 A1 | 8/2020 | Nitzan et al. |
| 2020/0269047 A1 | 8/2020 | Mazanec et al. |
| 2020/0315599 A1 | 10/2020 | Nae et al. |
| 2020/0330749 A1 | 10/2020 | Gribetz et al. |
| 2020/0368505 A1 | 11/2020 | Nae et al. |
| 2020/0376262 A1 | 12/2020 | Clark et al. |
| 2020/0391016 A1 | 12/2020 | Passman et al. |
| 2021/0007610 A1 | 1/2021 | Hendriks et al. |
| 2021/0008389 A1 | 1/2021 | Featherstone et al. |
| 2021/0023374 A1 | 1/2021 | Block et al. |
| 2021/0030273 A1 | 2/2021 | Huang et al. |
| 2021/0038230 A1 | 2/2021 | Larsen et al. |
| 2021/0046219 A1 | 2/2021 | Hendriks et al. |
| 2021/0052378 A1 | 2/2021 | Nitzan et al. |
| 2021/0085935 A1 | 3/2021 | Fahey et al. |
| 2021/0100513 A1 | 4/2021 | Sahmauyar et al. |
| 2021/0100665 A1 | 4/2021 | Nae et al. |
| 2021/0106281 A1 | 4/2021 | Tran |
| 2021/0121179 A1 | 4/2021 | Ben-david et al. |
| 2021/0121697 A1 | 4/2021 | Linde et al. |
| 2021/0145331 A1 | 5/2021 | Simpson et al. |
| 2021/0205590 A1 | 7/2021 | Fahey et al. |
| 2021/0212638 A1 | 7/2021 | Golda et al. |
| 2021/0252251 A1 | 8/2021 | Subramanian |
| 2021/0257849 A1 | 8/2021 | Keil et al. |
| 2021/0275805 A1 | 9/2021 | Boor et al. |
| 2021/0288527 A1 | 9/2021 | Bae et al. |
| 2021/0298763 A1 | 9/2021 | Stahmann et al. |
| 2021/0302751 A1 | 9/2021 | Brockman et al. |
| 2021/0353407 A1 | 11/2021 | Ma |
| 2021/0359550 A1 | 11/2021 | Budgett et al. |
| 2021/0361238 A1 | 11/2021 | Bak-Boychuk et al. |
| 2021/0361948 A1 | 11/2021 | Leuthardt et al. |
| 2021/0370032 A1 | 12/2021 | Fahey et al. |
| 2021/0401418 A1 | 12/2021 | Dang et al. |
| 2022/0008014 A1 | 1/2022 | Rowe et al. |
| 2022/0061679 A1 | 3/2022 | Adler et al. |

(56) References Cited

U.S. PATENT DOCUMENTS

| | | |
|---|---|---|
| 2022/0095992 A1 | 3/2022 | Guvenc et al. |
| 2022/0109402 A1 | 4/2022 | Gong et al. |
| 2022/0115187 A1 | 4/2022 | Kataky et al. |
| 2022/0117540 A1 | 4/2022 | Leuthardt et al. |
| 2022/0117555 A1 | 4/2022 | Zarbatauy et al. |
| 2022/0118251 A1 | 4/2022 | Buddha et al. |
| 2022/0131424 A1 | 4/2022 | Charthad et al. |
| 2022/0141663 A1 | 5/2022 | Kothandaraman et al. |
| 2022/0142652 A1 | 5/2022 | Alexander et al. |
| 2022/0151618 A1 | 5/2022 | Eigler et al. |
| 2022/0160309 A1 | 5/2022 | Poltorak |
| 2022/0167861 A1 | 6/2022 | Stahmann |
| 2022/0167921 A1 | 6/2022 | Aljuri et al. |
| 2022/0167922 A1 | 6/2022 | Gross et al. |
| 2022/0176120 A1 | 6/2022 | Kulkarni et al. |
| 2022/0176133 A1 | 6/2022 | Buddha et al. |
| 2022/0184355 A1 | 6/2022 | Fahey et al. |
| 2022/0192677 A1 | 6/2022 | Wedul et al. |
| 2022/0192819 A1 | 6/2022 | Rodeheaver et al. |
| 2022/0202505 A1 | 6/2022 | Roche |
| 2022/0218355 A1 | 7/2022 | Wedul et al. |
| 2022/0218964 A1 | 7/2022 | Fahey et al. |
| 2022/0226000 A1 | 7/2022 | Alexander et al. |
| 2022/0226156 A1 | 7/2022 | Lee et al. |
| 2022/0226623 A1 | 7/2022 | Fahey et al. |
| 2022/0233872 A1 | 7/2022 | Perryman et al. |
| 2022/0240856 A1 | 8/2022 | Stahmann et al. |
| 2022/0252849 A1 | 8/2022 | Lee et al. |
| 2022/0265157 A1 | 8/2022 | Charthad et al. |
| 2022/0265280 A1 | 8/2022 | Chamorro et al. |
| 2022/0266000 A1 | 8/2022 | Moffitt |
| 2022/0288401 A1 | 9/2022 | Landherr et al. |
| 2022/0300434 A1 | 9/2022 | Esteller |
| 2022/0313426 A1 | 10/2022 | Gifford, III et al. |
| 2022/0323781 A1 | 10/2022 | Subramanian et al. |
| 2022/0339448 A1 | 10/2022 | Jayakumar et al. |
| 2022/0362560 A1 | 11/2022 | Feldman |
| 2022/0378303 A1 | 12/2022 | Melodia et al. |
| 2022/0387785 A1 | 12/2022 | Huynh et al. |
| 2022/0387799 A1 | 12/2022 | Feldman et al. |
| 2022/0387806 A1 | 12/2022 | Mccormick et al. |
| 2022/0407360 A1 | 12/2022 | Chiao et al. |
| 2022/0413612 A1 | 12/2022 | Gribetz |
| 2023/0010306 A1 | 1/2023 | Bashirullah et al. |
| 2023/0041857 A1 | 2/2023 | Prutchi |
| 2023/0056111 A1 | 2/2023 | Gururaj et al. |
| 2023/0056924 A1 | 2/2023 | Fox et al. |
| 2023/0062862 A1 | 3/2023 | Forsell |
| 2023/0065828 A1 | 3/2023 | Forsell |
| 2023/0067764 A1 | 3/2023 | Forsell |
| 2023/0075205 A1 | 3/2023 | Moran et al. |
| 2023/0084193 A1 | 3/2023 | Fahey et al. |
| 2023/0118243 A1 | 4/2023 | Fox et al. |
| 2023/0129883 A1 | 4/2023 | Andriola et al. |
| 2023/0158280 A1 | 5/2023 | Andriola et al. |
| 2023/0181906 A1 | 6/2023 | Moore et al. |
| 2023/0198274 A1 | 6/2023 | Aghaeepour et al. |
| 2023/0201546 A1 | 6/2023 | Fahey et al. |
| 2023/0210374 A1 | 7/2023 | Charthad et al. |
| 2023/0211076 A1 | 7/2023 | Weber et al. |
| 2023/0218180 A1 | 7/2023 | Mujeeb-u-rahman et al. |
| 2023/0226344 A1 | 7/2023 | Richardson |
| 2023/0233229 A1 | 7/2023 | Picard et al. |
| 2023/0233849 A1 | 7/2023 | Gorski et al. |
| 2023/0238835 A1 | 7/2023 | Bae et al. |
| 2023/0264014 A1 | 8/2023 | Corey et al. |
| 2023/0277854 A1 | 9/2023 | Gavia |
| 2023/0329634 A1 | 10/2023 | Zaman |
| 2023/0346538 A1 | 11/2023 | Adler et al. |
| 2023/0355994 A1 | 11/2023 | Forsell |
| 2023/0355995 A1 | 11/2023 | Forsell |
| 2023/0364433 A1 | 11/2023 | Forsell |
| 2023/0364434 A1 | 11/2023 | Forsell |
| 2023/0371953 A1 | 11/2023 | Pantages et al. |
| 2023/0372683 A1 | 11/2023 | Andriola et al. |
| 2023/0405290 A1 | 12/2023 | Adriola et al. |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 2786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 103458832 | 12/2013 |
| CN | 105662653 | 6/2016 |
| CN | 109646063 A | 4/2019 |
| CN | 110536657 | 12/2019 |
| EP | 1583585 | 10/2005 |
| EP | 1112044 | 1/2007 |
| EP | 2022532 | 2/2009 |
| EP | 2082708 | 7/2009 |
| EP | 2097012 | 9/2009 |
| EP | 2277586 | 1/2011 |
| EP | 2528646 | 12/2012 |
| EP | 2630811 | 8/2013 |
| EP | 2642954 | 10/2013 |
| EP | 2967867 | 1/2016 |
| EP | 3087953 | 11/2016 |
| EP | 3185948 | 7/2017 |
| EP | 3291773 | 3/2018 |
| EP | 3329860 | 6/2018 |
| EP | 3347085 | 7/2018 |
| EP | 3400053 | 11/2018 |
| EP | 3474777 | 5/2019 |
| EP | 3487385 | 5/2019 |
| EP | 3520706 | 8/2019 |
| EP | 3551897 | 9/2019 |
| EP | 3541472 | 9/2019 |
| EP | 3589238 | 1/2020 |
| EP | 3692949 | 8/2020 |
| EP | 3704780 | 9/2020 |
| EP | 3723586 | 10/2020 |
| EP | 3740163 | 11/2020 |
| EP | 3777657 | 2/2021 |
| EP | 3777961 | 2/2021 |
| EP | 3813933 | 5/2021 |
| EP | 3912676 | 11/2021 |
| EP | 3997776 | 5/2022 |
| EP | 4114514 | 1/2023 |
| EP | 4138981 | 3/2023 |
| EP | 4204076 | 7/2023 |
| EP | 4228733 | 8/2023 |
| EP | 4243925 | 9/2023 |
| EP | 4252263 | 10/2023 |
| IL | 176973 | 12/2006 |
| IL | 221127 | 9/2012 |
| IL | 226374 | 7/2013 |
| IL | 215975 | 11/2016 |
| IL | 227756 | 6/2017 |
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2007527742 | 10/2007 |
| JP | 2010508093 | 3/2010 |
| JP | 2012196504 | 10/2012 |
| JP | 2013046784 | 3/2013 |
| JP | 2014503246 | 2/2014 |
| JP | 2014512869 | 5/2014 |
| JP | 2020509812 | 4/2020 |

(56) References Cited

FOREIGN PATENT DOCUMENTS

| | | |
|---|---|---|
| KR | 20010046155 | 6/2001 |
| WO | WO2005002467 | 1/2005 |
| WO | WO2005074367 | 8/2005 |
| WO | WO2007083288 | 7/2007 |
| WO | WO2008055301 | 5/2008 |
| WO | WO2008089726 | 7/2008 |
| WO | WO2010000026 | 1/2010 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014091222 | 6/2014 |
| WO | WO2014150106 | 9/2014 |
| WO | WO2014188279 | 11/2014 |
| WO | WO2016014821 | 1/2016 |
| WO | WO2016038115 | 3/2016 |
| WO | WO2016178171 | 11/2016 |
| WO | WO2017136767 | 8/2017 |
| WO | WO2017139606 | 8/2017 |
| WO | WO2017151566 | 9/2017 |
| WO | WO2017207981 | 12/2017 |
| WO | WO2017214740 | 12/2017 |
| WO | WO2018024868 | 2/2018 |
| WO | WO2018154138 | 3/2018 |
| WO | WO2018132549 | 7/2018 |
| WO | WO2018158747 | 9/2018 |
| WO | WO2019025785 | 2/2019 |
| WO | WO2019142152 | 7/2019 |
| WO | WO2019175401 | 9/2019 |
| WO | WO2019183078 | 9/2019 |
| WO | WO2020023514 | 1/2020 |
| WO | WO2020110048 | 6/2020 |
| WO | WO2020123338 | 6/2020 |
| WO | WO2020142515 | 7/2020 |
| WO | WO2020142613 | 7/2020 |
| WO | WO2020198694 | 10/2020 |
| WO | WO2020202046 | 10/2020 |
| WO | WO2020206366 | 10/2020 |
| WO | WO2020217194 | 10/2020 |
| WO | WO2020225757 | 11/2020 |
| WO | WO2020234751 | 11/2020 |
| WO | WO2021050589 | 3/2021 |
| WO | WO2021061272 | 4/2021 |
| WO | WO2021072315 | 4/2021 |
| WO | WO2021159001 | 8/2021 |
| WO | WO2021212011 | 10/2021 |
| WO | WO2021216964 | 10/2021 |
| WO | WO2021217055 | 10/2021 |
| WO | WO2021217059 | 10/2021 |
| WO | WO2021252397 | 12/2021 |
| WO | WO2022043555 | 3/2022 |
| WO | WO2022046921 | 3/2022 |
| WO | WO2022076601 | 4/2022 |
| WO | WO2022081980 | 4/2022 |
| WO | WO2022103973 | 5/2022 |
| WO | WO2022165320 | 8/2022 |
| WO | WO2022192280 | 9/2022 |
| WO | WO2022197748 | 9/2022 |
| WO | WO2022261492 | 12/2022 |
| WO | WO2022266465 | 12/2022 |
| WO | WO2022266503 | 12/2022 |
| WO | WO2022269278 | 12/2022 |
| WO | WO2022272131 | 12/2022 |
| WO | WO2023278612 | 1/2023 |
| WO | WO2023278725 | 1/2023 |
| WO | WO2023280858 | 1/2023 |
| WO | WO2023026124 | 3/2023 |
| WO | WO2023028164 | 3/2023 |
| WO | WO2023031039 | 3/2023 |
| WO | WO2023097337 | 6/2023 |
| WO | WO2023141266 | 7/2023 |
| WO | WO2023156529 | 8/2023 |
| WO | WO2023177690 | 9/2023 |
| WO | WO2023183417 | 9/2023 |

OTHER PUBLICATIONS

Abidin et al., "Design of Interdigital Structured Supercapacitor for Powering Biomedical Devices," 2011 IEEE Regional Symposium on Micro and Nano Electronics, pp. 88-91, Sep. 28-30, 2011, 4 pages.

Abidin et al., "Interdigitated MEMS Supercapacitor for Powering Heart Pacemaker," InTech, Nov. 2, 2016, 21 pages.

Aqueveque et al., "Wireless power system for charge supercapacitors as power sources for implantable devices," 2015 IEEE Pels Workshop on Emerging Technologies: Wireless Power (2015 WoW), Daejeon, South Korea, pp. 1-5, Jun. 5, 2015, 5 pages.

Baker, "New Mesh Technology Helps Holds Down Infection Rates in Pacemakers," KERA News, Jul. 29, 2019, 3 pages.

Chae et al., "A durable high-energy implantable energy storage system with binder-free electrodes useable in body fluids," Journal of Materials Chemistry A, Feb. 1, 2022, 11 pages.

Chae et al., "Electrode materials for biomedical patchable and implantable energy storage devices," Energy Storage Materials, vol. 24, pp. 113-128, Apr. 24, 2019, 16 pages.

Chen et al., "Stretchable Supercapacitors as Emergent Energy Storage Units for Health Monitoring Bioelectronics," Advanced Healthcare Materials, Dec. 10, 2019, 27 pages.

DeLong et al., "Wireless Energy Harvesting for Medical Applications," 2015 IEEE International Symposium on Antennas and Propagation & USNC/URSI National Radio Science Meeting, Vancouver, BC, Canada, Jul. 19-24, 2015, 1 page.

Fadhel et al., "Resonant Inductive Coupling for Wirelessly Powering Active Implants: Current Issues, Proposed Solutions and Future Technological attempts," Advanced Systems for Biomedical Application, Smart Sensors, Measurement and Instrumentation, vol. 39, Jul. 20, 2021, 37 pages.

Gall et al., "A Batteryless Energy Harvesting Storage System for Implantable Medical Devices Demonstrated in Situ," Circuits, Systems, and Signal Processing, Aug. 11, 2018, 14 pages.

Guida et al., "A 700 kHz Ultrasonic Link for Wireless Powering of Implantable Medical Devices," 2016 IEEE Sensors Conference, Oct. 30, 2016, 3 pages.

Guida et al., "Ultrasonically Rechargeable Platforms for Closed-Loop Distributed Sensing and Actuation in the Human Body," 2018 IEEE 19th International Workshop on Signal Processing Advances in Wireless Communications (SPAWC), Kalamata, Greece, 2018, pp. 1-5, Jun. 25-28, 2018, 5 pages.

He et al., "Biocompatible carbon nanotube fibers for implantable supercapacitors," Carbon, vol. 122, pp. 162-167, Oct. 2017, 6 pages.

Hu et al., "Wireless Power Supply for ICP Devices With Hybrid Supercapacitor and Battery Storage," IEEE Journal of Emerging and Selected Topics in Power Electronics, vol. 4, No. 1, pp. 273-279, Mar. 2016, 7 pages.

Kassanos et al., "Power and data communication in wearable and implantable devices," Wearable Sensors (Second Edition), pp. 279-309, Jan. 1, 2021, 31 pages.

Kim et al., "New and Emerging Energy Sources for Implantable Wireless Microdevices," IEEE Access, vol. 3, pp. 89-98, Feb. 23, 2015, 10 pages.

Lamberti et al., "TiO2 nanotube array as biocompatible electrode in view of implantable supercapacitors," Journal of Energy Storage, vol. 8, pp. 193-197, Aug. 27, 2016, 5 pages.

Lv et al., "A Degradable and Biocompatible Supercapacitor Implant Based on Functional Sericin Hydrogel Electrode," Advanced Materials Technologies, Mar. 2, 2023, 10 pages.

Mahesh et al., "Design Analysis of Defibrillator and Implementing Wireless Charging System," 2020 5th International Conference on Communication and Electronics Systems (ICCES), pp. 295-299, Jun. 10-12, 2020, 5 pages.

Mendoza-Ponce et al., "Super-capacitors for implantable medical devices with wireless power transmission," 2018 14th Conference

(56) References Cited

OTHER PUBLICATIONS on Ph.D. Research in Microelectronics and Electronics (Prime), Prague, Czech Republic, 2018, pp. 241-244, Jul. 2-5, 2018, 4 pages.
Meng et al., "A flexible super-capacitive solid-state power supply for miniature implantable medical devices," Biomed Microdevices, Jul. 9, 2013, 11 pages.
Meng et al., "Ultrasmall Integrated 3D Micro-Supercapacitors Solve Energy Storage for Miniature Devices," Advanced Energy Materials, Dec. 12, 2013, 7 pages.
Monti et al., "Resonant Inductive Link for Remote Powering of Pacemakers," IEEE Transactions on Microwave Theory and Techniques, vol. 63, No. 11, pp. 3814-3822, Nov. 2015, 9 pages.
Mosa et al., "Ultrathin Graphene-Protein Supercapacitors for Miniaturized Bioelectronics," Advanced Energy Materials, Sep. 6, 2017, 21 pages.
Pandey et al., "Integration of Supercapacitors into Wirelessly Charged Biomedical Sensors," 2011 6th IEEE Conference on Industrial Electronics and Applications, Beijing, China, Jun. 21-23, 2011, pp. 56-61, 6 pages.
Park et al., "An implantable anti-biofouling biosupercapacitor with high energy performance," Biosensors and Bioelectronics, May 30, 2023, 16 pages.
Rabin et al., "Operability of Implantable Integrated Implants' Wireless Charging Device and Biotelemetric System," 2019 25th Conference of Open Innovations Association (FRUCT), Helsinki, Finland, 2019, pp. 257-264, Nov. 5-8, 2019, 8 pages.
Rita et al., "Effect of Supercapacitor on Power Supply for Rechargeable Implanted Medical Devices," Recent Innovations in Computing, ICRIC 2020, Lecture Notes in Electrical Engineering, vol. 701, pp. 123-134, Springer Nature Singapore Pte Ltd., Jan. 13, 2021, 12 pages.
Sanchez et al., "An Energy Management IC for Bio-Implants Using Ultracapacitors for Energy Storage," 2010 Symposium on VLSI Circuits, Jun. 15-17, 2010, 2 pages.
Sheng et al., "A soft implantable energy supply system that integrates wireless charging and biodegradable Zn-ion hybrid supercapacitors," Science Advances, Nov. 15, 2023, 17 pages.
Sheng et al., "A thin, deformable, high-performance supercapacitor implant that can be biodegraded and bioabsorbed within an animal body," Science Advances, Jan. 8, 2021, 11 pages.
Sheng et al., "Recent Advances of Energy Solutions for Implantable Bioelectronics," Advanced Healthcare Materials, Apr. 30, 2021, 25 pages.
Sim et al., "Biomolecule based fiber supercapacitor for implantable device," Nano Energy, vol. 47, pp. 385-392, May 2018, 8 pages.
Skunik-Nuckowska et al., "Integration of supercapacitors with enzymatic biobatteries toward more effective pulse-powered use in small-scale energy harvesting devices," Journal of Applied Electrochemistry, vol. 44, pp. 497-507, Jan. 4, 2014, 11 pages.
Su et al., "Stretchable Transparent Supercapacitors for Wearable and Implantable Medical Devices," Advanced Materials Technologies, Sep. 23, 2021, 6 pages.
Tian et al., "Implantable and Biodegradable Micro-Supercapacitor Based on a Superassembled Three-Dimensional Network Zn@PPy Hybrid Electrode," ACS Applied Materials Interfaces, Feb. 14, 2021, 10 pages.
Tran et al., "A compact wireless power transfer system at 915 MHz with supercapacitor for optogenetics applications," Sensors and Actuators A: Physical, Nov. 20, 2018, 9 pages.
Ungureanu et al., "Using of ISM radio bands for wireless charging of medical implants," 9th International Conference on Microelectronics and Computer Science, Chisinau, Republic of Moldova, Oct. 19-21, 2017, 4 pages.
Vanderbilt Heart and Vascular Institute, "'Envelope' reduces cardiac implant infections," VUMC Reporter, Aug. 8, 2013, retrieved from website <URL: http://news.vanderbilt.edu/2013/08/envelop-reduces-cardiac-implant-infections/resorbablecardiac-implant>, 2 pages.
Wu et al., "Subcutaneous Solar Energy Harvesting for Self-Powered Wireless Implantable Sensor Systems," 2018 40th Annual International Conference of the IEEE Engineering in Medicine and Biology Society (EMBC), Honolulu, HI, USA, pp. 4657-4660, Jul. 18-21, 2018, 4 pages.
Xu et al., "Minimally invasive power sources for implantable electronics," Exploration, Jun. 8, 2023, 20 pages.
Extended European Search Report received for Application No. 21793483.5, Applicant: Shifamed Holdings, LLC; Date of Mailing: Apr. 18, 2024; 11 pages.
International Search Report and Written Opinion received for International Application No. PCT/US22/19374, filed Mar. 8, 2022; Applicant: Shifamed Holdings, LLC; Date of Mailing: Jun. 24, 2022; 11 pages.
International Search Report and Written Opinion received for International Application No. PCT/US22/35764, filed Jun. 30, 2022; Applicant: Shifamed Holdings, LLC; Date of Mailing: Sep. 19, 2022; 10 pages.
Ando et al., "Left ventricular decompression through a patent foramen ovale in a patient with hypertrophic cardiomyopathy: a case report," Cardiovascular Ultrasound Volume, Article No. 2 (2004).
Braunwald, Heart Disease, Chapter 6, 2015, p. 186.
Bridges et al., "The Society of Thoracic Surgeons practice guideline series: transmyocardial laser revascularization," The Annals of Thoracic Surgery, vol. 77, Issue 4, Apr. 2004, pp. 1494-1502.
Bristow et al., "Improvement in cardiac myocyte function by biological effects of medical therapy: A new concept in the treatment of heart failure," European Heart Journal, vol. 16, Issue suppl. F, Jul. 1995, pp. 20-31.
Case et al., "Relief of High Left-Atrial Pressure in Left-Ventricular Failure," Lancet, Oct. 17, 1964, pp. 841-842.
Coats et al., "Controlled trial of physical training in chronic heart failure. Exercise performance, hemodynamics, ventilation, and autonomic function," Circulation, 1992;85:2119-2131.
Davies et al., "Reduced contraction and altered frequency response of isolated ventricular myocytes from patients with heart failure," Circulation, (1995), 92:2540-2549, Circulation, (1995), 92:2540-2549.
Ennezat et al., "An unusual case of low-flow, low gradient severe aortic stenosis: Left-to-right shunt due to atrial septal defect," Cardiology, (2009), 113(2):146-148.
Ewert et al., "Masked Left Ventricular Restriction in Elderly Patients With Atrial Septal Defects: A Contraindication for Closure," Catheterization and Cardiovascular Interventions, 52: 177-180, 2001.
Ewert et al., "Acute left heart failure after interventional occlusion of an atrial septal defect," Z. Kardiol., Catheterization and Cardiovascular Interventions, Z. Kardiol., (May 2001), 90(5):362-366.
Geiran et al., "Changes in cardiac dynamics by opening an interventricular shunt in dogs," J. Surg. Res., (Jan. 1990), 48(1):6-12.
Gelernter-Yaniv et al., "Transcatheter closure of left-to-right interatrial shunts to resolve hypoxemia," Congenit. Heart Dis., (Jan. 2008), 31(1):47-53.
Gewillig et al., "Creation with a stent of an unrestrictive lasting atrial communication," Cardio. Young, (2002), 12(4):404-407.
Khositseth et al., "Transcatheter Amplatzer Device Closure of Atrial Septal Defect and Patent Foramen Ovale in Patients With Presumed Paradoxical Embolism," Mayo Clinic Proc., 79:35-41 (2004).
Kramer et al., "Controlled study of captopril in chronic heart failure: A rest and exercise hemodynamic study," Circulation, (1983), 67(4):807-816.
Lai et al., "Bidirectional shunt through a residual atrial septal defect after percutaneous transvenous mitral commissurotomy," Cardiology, (1993), 83(3):205-207.
Lemmer et al., "Surgical implications of atrial septal defect complicating aortic balloon valvuloplasty," Ann. thorac. Surg., (Aug. 1989), 48(2):295-297.
Park et al., "Blade atrial septostomy: collaborative study," Circulation, 66(2):258-266 (1982).
Roven et al., "Effect of Compromising Right Ventricular Function in Left Ventricular Failure by Means of Interatrial and Other Shunts," American Journal Cardiology, 24:209-219 (1969).

(56) References Cited

OTHER PUBLICATIONS

Salehian et al., "Improvements in Cardiac Form and Function After Transcatheter Closure of Secundum Atrial Septal Defects," Journal of the American College of Cardiology, 45(4):499-504 (2005).
Schmitto et al., "Chronic heart failure induced by multiple sequential coronary microembolization in sheep," The International Journal of Artificial Organs, 31(4):348-353 (2008).
Schubert et al., "Left ventricular conditioning in the elderly patient to prevent congestive heart failure after transcatheter closure of the atrial septal defect," Catheter Cardiovasc. Interv., (2005), 64(3):333-337.
Stormer et al., "Comparative study of in vitro flow characteristics between a human aortic valve and a designed aortic and six corresponding types of prosthetic heart valves," European Surgical Research, (1976), 8(2):117-131.
Stumper et al., "Modified technique of stent fenestration of the atrial septum, Heart," (2003), 89:1227-1230.
Trainor et al., "Comparative Pathology of an Implantable Left Atrial Pressure Sensor," ASAIO Journal, Clinical Cardiovascular/Cardiopulmonary Bypass, 59(5):486-92 (2013).
Zhou et al., "Unidirectional valve patch for repair of cardiac septal defects with pulmonary hypertension," Annals of Thoracic Surgeons, 60: 1245-1249, 1995.
Jodi Perkins, "Corvia Medical and physIQ Partner in Global Phase 3 Heart Failure Clinical Trial to Leverage Novel Digital Endpoints," Press Release, 2019 Copyright, Medical Alley Association, 3 pages.
Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.
International Search Report and Written Opinion received for International Application No. PCT/US20/49996 filed Sep. 9, 2020; Applicant: Shifamed Holdings, LLC; Date of Mailing: Feb. 17, 2021; 16 pages.
International Search Report and Written Opinion received for International Application No. PCT/US20/063360 filed Dec. 4, 2020; Applicant: Shifamed Holdings, LLC; Date of Mailing: Apr. 5, 2021; 13 pages.
International Search Report and Written Opinion received for International Application No. PCT/US20/64529 filed Dec. 11, 2020; Applicant: Shifamed Holdings, LLC; Date of Mailing: Apr. 8, 2021; 12 pages.
International Search Report and Written Opinion received for International Application No. PCT/US19/68354, filed Dec. 23, 2019; Applicant: Shifamed Holdings, LLC; Date of Mailing: Mar. 17, 2020; 11 pages.
International Search Report and Written Opinion received for International Application No. PCT/US21/16932, filed Feb. 5, 2021; Applicant: Shifamed Holdings, LLC; Date of Mailing: Jun. 3, 2021; 11 pages.
International Search Report and Written Opinion received for International Application No. PCT/US21/14433, filed Jan. 21, 2021; Applicant: Shifamed Holdings, LLC; Date of Mailing: May 14, 2021; 16 pages.
International Search Report and Written Opinion received for International Application No. PCT/US21/28926, filed Apr. 23, 2021; Applicant: Shifamed Holdings, LLC; Date of Mailing: Jul. 22, 2021; 16 pages.
International Search Report and Written Opinion received for International Application No. PCT/US19/69106 filed Dec. 31, 2019; Applicant: Shifamed Holdings, LLC; Date of Mailing: Mar. 23, 2020; 10 pages.
International Search Report and Written Opinion received for International Application No. PCT/US22/34027, filed Jun. 17, 2022; Applicant: Shifamed Holdings, LLC; Date of Mailing: Oct. 25, 2022; 8 pages.
International Search Report and Written Opinion received for International Application No. PCT/US22/34995, filed Jun. 24, 2022; Applicant: Shifamed Holdings, LLC; Date of Mailing: Nov. 18, 2022; 17 pages.
Perk et al., "Catheter-based left atrial appendage occlusion procedure: role of echocardiography," published on behalf of the European Society of Cardiology, Sep. 8, 2011, 7 pages.
Collado et al, "Left Atrial Appendage Occlusion for Stroke Prevention in Nonvalvular Atrial Fibrillation," Journal of the American Heart Association, Jun. 2021, 18 pages.
International Search Report and Written Opinion received for International Application No. PCT/US21/28931, filed Apr. 23, 2021; Applicant: Shifamed Holdings, LLC; Date of Mailing: Sep. 24, 2021; 20 pages.
International Search Report and Written Opinion received for International Application No. PCT/US21/27747, filed Apr. 16, 2021; Applicant: Shifamed Holdings, LLC; Date of Mailing: Oct. 1, 2021; 16 pages.
International Search Report and Written Opinion received for International Application No. PCT/US20/12059, filed Jan. 2, 2020; Applicant: Shifamed Holdings, LLC; Date of Mailing: Jun. 5, 2020; 12 pages.
International Search Report and Written Opinion received for International Application No. PCT/US20/25509, filed Mar. 27, 2020; Applicant: Shifamed Holdings, LLC; Date of Mailing: Jun. 25, 2020; 9 pages.
International Search Report and Written Opinion received for International Application No. PCT/US20/26738, filed Apr. 3, 2020; Applicant: Shifamed Holdings, LLC; Date of Mailing: Jun. 30, 2020; 8 pages.

\* cited by examiner

INTERNAL RECHARGING SYSTEMS AND METHODS OF USE

CROSS-REFERENCE TO RELATED APPLICATION(S)

This application is a 35 U.S.C. § 371 U.S. National Phase application of International Patent Application No. PCT/US2020/012059, filed Jan. 2, 2020, which claims priority to U.S. Provisional Application 62/788,642, filed Jan. 4, 2019, the disclosures of which are incorporated herein by reference in their entireties.

INCORPORATION BY REFERENCE

This application claims priority to U.S. Provisional Application 62/788,642, filed Jan. 4, 2019, which is incorporated by reference herein for all purposes.

All publications and patent applications mentioned in this specification are herein incorporated by reference for all purposes to the same extent as if each individual publication or patent application was specifically and individually indicated to be incorporated by reference. The entire disclosure in U.S. Pat. No. 8,593,107 is incorporated by reference herein for all purposes.

BACKGROUND

Implantable sensors can be used within the human body to measure a number of physiological parameters and enhance diagnostic and treatment paradigms. For example, sensors may be adapted to measure a patient's ECG, blood pressure in various locations, cardiac output, insulin levels, and other parameters of interest.

Implanted sensors are often considered permanent, and several factors may make the retrieval of an implant impractical or inadvisable. Therefore, an implant should be configured to remain functional for an extended period of time.

Power management is a key component of virtually any implanted sensor system. Even for low-power miniaturized devices, some degree of power is generally required to capture measurements, optionally store information in local memory, and transmit information outward to a data reader via an antenna. Many systems obviate the need for a battery via the use of a passive design, where the sensor is activated by an externally applied signal (for example, an RF signal) that interrogates the device and creates a return signal that sends the measurement outward to a reader. However, there are advantages to the use of an active (i.e. powered by a battery or other longer-term energy storage device such as a super capacitor) system, and in some applications a battery-powered system may be required to achieve critical device functionality.

A method known in the art to address the balance between the desire for an active system and the desire for long device lifespan is the use of a rechargeable system, such as one that includes a rechargeable device, such as a battery, rechargeable super capacitor, or similar device. Rechargeable batteries may be actively recharged using a variety of internal or external means, such as by harvesting energy from applied (e.g., a transmitted radiofrequency signal) or natural (e.g., the mechanical motion of a body part) sources. However, charging methodologies remain challenging for certain types of implanted sensors due to issues such as tissue overgrowth and endothelialization. Improved devices, systems and methods are needed.

SUMMARY

One aspect of the disclosure is a catheter adapted for transmitting energy to an implantable sensing device, comprising: an energy transmission region in a distal region of the catheter, the energy transmission region including at least one transducer. The catheter may also include an expandable stabilization member in the distal region of the catheter, the stabilization member adapted and configured to be expanded radially outward relative to a shaft of the catheter and into contact with a vessel in which the catheter is positioned to stabilize the transducer.

One aspect of the disclosure is a method of stabilizing a recharging catheter, comprising: positioning an energy transmission region of a recharging catheter adjacent a sensing implant in a blood vessel through which blood is flowing, the sensing implant including a sensor, at least one receive transducer, and a rechargeable power source (e.g., battery, supercapacitor), the energy transmission region including at least one emit transducer. The method can include expanding a stabilization member radially outward relative to a shaft of the recharging catheter to increase the stability of the at least one emit transducer relative to the receive transducer.

One aspect of the disclosure is a system for recharging an implantable sensing device, comprising: a sensing implant comprising a plurality of receive transducers, the plurality of receive transducers spaced from one another; and a recharging catheter comprising one or more emit transducers. The one or more emit transducers may be a plurality of emit transducers that are spaced from one another.

One aspect of the disclosure is a system for recharging a sensing implant while actively reducing heating of tissue, comprising: a recharging catheter with one or more emit transducers in a distal region; an energy controller in operable communication with the one or more emit transducers, the energy controller adapted to control the path of energy emitted from the one or more emit transducers to selectively deliver energy from the one or more emit transducers to one of a plurality of receive transducers of a sensing implant to actively reduce heating of tissue over the sensing implant while charging the sensing implant.

One aspect of the disclosure is an implantable sensing device comprising a plurality of receive transducers, the plurality of receive transducers spaced apart from one another (e.g. sensor implant 200 with transducers 201).

DETAILED DESCRIPTION

Figures 1A, 1B:
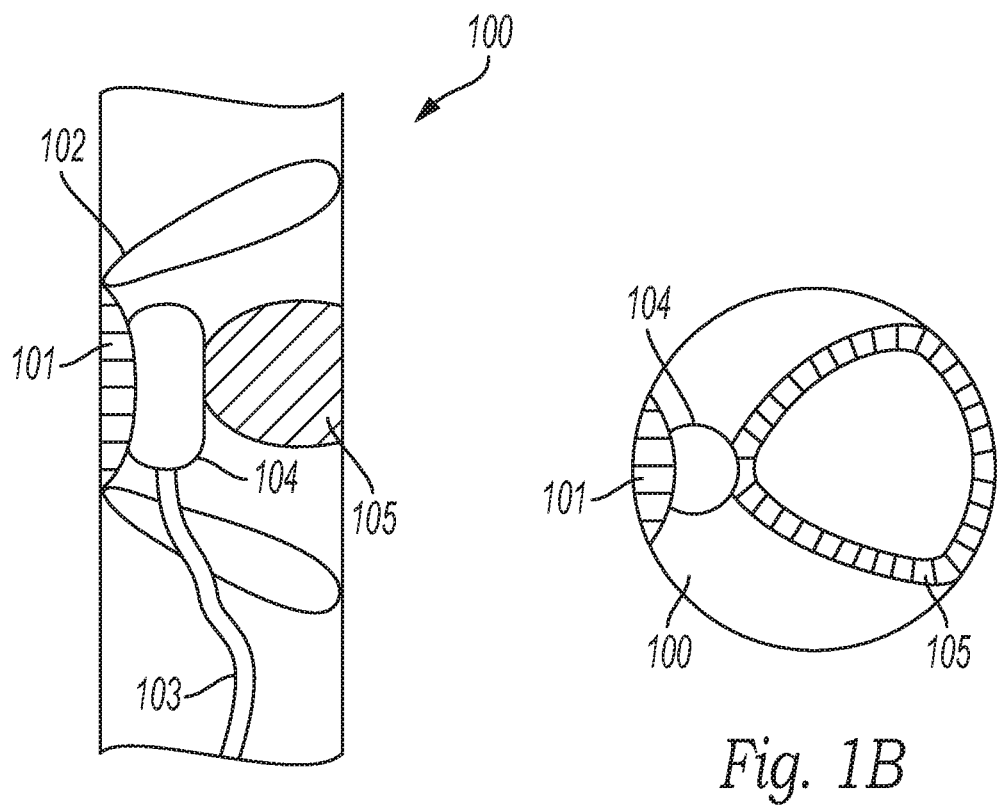
FIG. 1A is a side view of an exemplary recharging catheter recharging an implanted sensor implant.
FIG. 1B is an end view of an exemplary recharging catheter recharging an implanted sensor implant.

In general, the implanted systems described herein include at least a sensor implant with a rechargeable battery, and a catheter-based recharging interface. In methods of use, during recharging, the catheter is inserted into the vasculature of the patient and navigated to a region proximate to the sensor implant location, at which point the recharging components of the catheter may be activated in order to deliver energy to the rechargeable battery of the sensor implant. It should be noted that while the present disclosure focuses on systems that utilize a battery, the inventions described herein may be applied to related systems (for example, those which use a super capacitor instead of or in addition to a battery). It is thus understood that a battery is merely an exemplary rechargeable power source, and when an embodiment includes a battery, it is understood that a different power source can be used instead, unless specifically indicated to the contrary.

In some embodiments, the recharging paradigm involves magnetic power coupling. In such systems, an implanted device may be comprised of components including a sensor configured to be responsive to a body parameter, an antenna adapted for transferring information to a remote receiver, a rechargeable battery, an anchoring mechanism, a magnetic docking interface, circuitry and/or electronics associated with receiving an external source of electromagnetic energy, and an enclosure or housing to protect and/or isolate certain components from the body environment. In these exemplary systems, the recharging catheter may include a proximal end and a distal end, with the proximal end including one or more of the following: a handle, various connections to external power supplies or adapters, and various user control features such as buttons, toggles, and mechanical manipulation tools such as dials or pulleys. A flexible and elongated catheter body connects the proximal and distal end regions of the catheter, the catheter body comprising one or more lumens to allow the catheter to interface with, for example, a guidewire and other related accessory components known to those skilled in the art. The distal end of the catheter can include a magnetic docking interface (of opposite polarity of the interface on the sensor implant) and driving electronics to emit/transfer an electromagnetic signal from the catheter to the sensing implant battery in order to recharge the sensor implant battery. In some implementations, the catheter and/or sensor may include a ferromagnetic material that may assist with one or more of a process of docking, a process of recharging, for other purposes, or for multiple purposes.

In various embodiments, in lieu of or in addition to a magnetic docking interface, the catheter includes an expandable stabilization member, such as an expandable balloon, or other expandable member such as a stent or stent-like device, to hold it (maintain its position) proximate to the recharging circuitry of the implant in order to facilitate a transfer of energy. In preferred implementations, the stabilization member comprises a compliant balloon constructed of silicone, latex, or a similar material. In some methods of use, the catheter is navigated toward the location of the sensor implant, and the catheter position is manipulated such that the distal tip of the catheter is in a proper or desired physical position relative to the implant. In some embodiments, this can be accomplished by visual inspection using image guidance such as fluoroscopy. In some embodiments this can be accomplished using magnetic sensors or other circuitry that detects the presence of metal in the implant, or another feature of the implant. In further variations the tip of the catheter may emit and or receive a signal, for example a laser, ultrasound, or IR signal, that can detect the presence of a strong signal reflector in the line of transmission. In some embodiments, the desired physical position of the catheter is with the distal tip proximate to the sensor. In other embodiments, the desired physical position of the catheter is with the catheter tip distally beyond the location of the sensor (and optionally beyond a distal end of the sensor implant) and a selected portion of the catheter body proximate to the sensor. This latter configuration may allow for additional features to be deployed downstream of the implant location, for example embolic protection features such as temporarily deployable blood clot filter, which may be incorporated into the catheter or part of a different device.

In some embodiments, the sensor implant may be located inside or proximate to a blood vessel, and therefore the recharging catheter may be required to be disposed within the vessel during the recharging process. In embodiments in which the anchoring member comprises an inflatable member (e.g. an inflatable/expandable membrane), the inflation of a standard single-lumen stabilization balloon may be impractical as it may lead to prolonged occlusion of the vessel. Instead, multi-lumen balloons, balloons shaped as cylindrical tubes, and similar implementations may be desirable to prevent prolonged occlusion of the vessel. Any of the balloons herein can be configured and/or sized so as not to occlude blood flow. FIGS. 1A and 1B illustrate an exemplary recharging system, including an expandable stabilization member, wherein the expandable stabilization member is sized and configured so as not to completely occlude the flow of blood in the lumen when inflated. FIG. 1A is a side view (long axis view) of the system disposed in a blood vessel lumen 100 with stabilization balloon 105 inflated. FIG. 1B is an end view of the system and lumen 100, with the lumen wall generally circular in cross section as shown in FIG. 1B. As shown in FIGS. 1A and 1B sensor implant 101 is held in place (anchored) via a plurality of implant vessel anchors 102. Distal end 104 of catheter 103 (which includes an outer shaft) is shown interfacing with implant 101 in a position where recharging of a battery may occur. Stabilization balloon 105 has been inflated and presses against the vessel wall in order to press and hold or maintain the catheter distal end 104 against the implant 101. As shown in the end view of FIG. 1B, balloon 105 is hollow in nature, allowing blood flow to travel through the vessel while the balloon is deployed without significant resistance or occlusion.

In other embodiments, implant anchors (such as anchors 102) are adapted and configured as annular antennae, in addition to functioning as sensing implant anchors.

In some embodiments, the recharging paradigm involves ultrasonic or otherwise acoustic-based recharging. Acoustic charging involves focusing a mechanical pressure wave onto a piezoelectric material or other electro-mechanical transducer, which converts the incident pressure into an electrical output. Although acoustic energy transfer paradigms have been previously disclosed, they often involve transducers placed outside of the body that send acoustic energy across soft tissues into receiving transducers. In these previously disclosed methods, the acoustic signals are substantially attenuated as they traverse tissues to reach the target, resulting in both signal loss and raising the possibility of unwanted tissue heating along the acoustic pathway.

In some preferred embodiments, a catheter is adapted to deliver ultrasonic energy directly to a sensor implant that is configured to receive such energy in order to recharge a battery (or other rechargeable power source). In some methods of use, the ultrasound catheter is navigated into position using any methods described herein or incorporated by reference herein. In some embodiments, the ultrasound catheter may be configured to operate in an imaging mode, which assists with navigation to a target location in proximity to the sensing implant to be recharged. When the catheter is in the desired position, ultrasound energy may be directed from the catheter and toward the desired portion of the sensor implant in order to induce an electrical current that may be used to recharge a battery in the sensor implant. In some preferred embodiments, the emission transducer on the catheter delivers high frequency (e.g. >10 MHz) energy using continuous wave (CW) operation or transmissions with a high duty cycle. The emission transducer may be focused or unfocused, and if focused, focusing can be accomplished via mechanical, phasing, or other means.

A challenge with ultrasound recharging (and possibly other types of charging, including magnetic/EM charging) is related to the tissue overgrowth that is anticipated to encompass the sensor over time due to the process of endothelialization. Tissue overgrowth presents a barrier that will cause losses and attenuation of the delivered ultrasound energy, which will increase the period of time required to achieve recharging. Perhaps more importantly, due to these losses, heat will accumulate in this tissue region, especially during ultrasonic transmission paradigms (i.e., CW or high duty cycle) that are desirable during recharging. Elevated tissue temperatures could lead to thermal ablation of tissue due to protein denaturation and associated necrosis. A mass of dead tissue on top of the implant may pose various safety risks, including the potential for emboli during the subsequent immune response.

Accordingly, preferred battery recharging methods and systems will be adapted to limit temperature rise in tissues that may overgrow upon the sensor implant and other surrounding tissues. Some methods and devices may limit this temperature rise to less than 6° C., and some methods and devices may limit the temperature rise to less than 1° C. In some embodiments, temperature rises are limited by adjusting one or more of the output power, duty cycle, or other characteristics of the ultrasound beam based upon assumed tissue properties, for example, as modeled by the Bioheat Transfer equation or other suitable methods known to those skilled in the art. In some embodiments, temperature rises in overgrowth or other tissue regions are monitored (for example using IR thermometer methods, or ultrasonic thermal strain methods) and alterations to the delivery of charging energy are made in response to the detection of a notable temperature rise, for example a temperature rise of 2° C. In some embodiments, methods can include (and devices adapted with) feedback mechanisms to change one or more delivery parameters of the charging energy if a sensed temperature rise is above a threshold rise. In some embodiments, methods can include (and devices adapted with) feedback mechanisms to change one or more delivery parameters of the charging energy to stop an increase in tissue rise, and optionally cause the tissue temperature to be lowered, optionally below a threshold. In some embodiments, methods can include (and devices adapted with) feedback mechanisms (e.g., algorithms stored in an external device) to change one or more delivery parameters of the charging energy to maintain an increase in tissue temperature below a threshold increase (some tissue heating may occur, but an increase above a threshold limit is prevented). The methods can monitor for temperatures and/or increases in temperatures. For example, the methods can compare a sensed tissue temperature with a threshold temperature, and/or the methods can monitor for a certain increase in tissue temperature.

Figure 2:
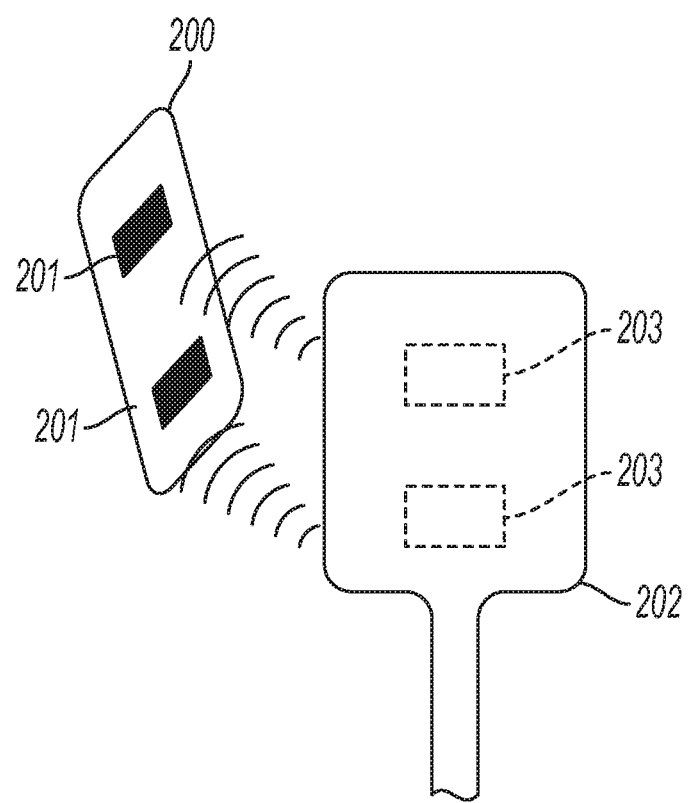
FIG. 2 illustrates energy being transmitted from an exemplary distal region of a recharging catheter to an exemplary implanted sensing device.

In some embodiments, temperature rises in overgrowth tissue are limited by using a plurality of charging interface locations. FIG. 2 illustrates an exemplary embodiment with two such interface locations. A sensor implant 200 includes two piezoelectric transducers 201 that are adapted to receive ultrasonic energy in order to recharge a battery, which is not shown for clarity. Sensor implant 200 can include any other component from any other sensor implant shown or described herein (e.g. anchors such as those shown in FIG. 1A). Receiving transducers 201 are spaced apart from one another and in this embodiment are disposed on opposite ends of the sensor implant 200, and spaced apart by a distance that is greater, and preferably much greater, than the width of the incident ultrasound beam utilized to deliver energy for recharging. The distal end of the recharging catheter 202 (optionally a distal tip) includes a plurality of ultrasound transducers 203, two in this embodiment, that can be adapted to deliver energy (shown as waves in FIG. 2) to the sensor implant. In an exemplary method of use, the ultrasound transducer 203 at the top in FIG. 2 may initially deliver recharging energy to the corresponding top piezoelectric receiver 201 either for a set period of time or until a pre-determined degree of temperature rise is noted in tissue near the top receiver. At that time, the transmission from the top transducer can cease and, with or without a pause or delay, the bottom ultrasound transducer 203 can begin transmitting energy directed toward the bottom piezoelectric receiver 201 on the sensor implant. By stopping/pausing the energy delivery to the top transducer, tissue in the region near the top piezoelectric receiver can cool during the period where it is not being actively exposed to ultrasonic energy. After a predetermined period of time or after a pre-determined degree of temperature rise is noted in tissue near the bottom receiver, the active transmission/receive pair will toggle once again, with the top transducer on the catheter transmitting energy. This process can repeat until the battery recharging process is complete. Cycling between energy transmission from the one or more transducers 203 can be an automated process (e.g., pre-set time periods, or automatic sensing/monitoring of tissue temps and automatically stopping energy delivery), or in some scenarios it may include one or more manual steps.

An exemplary benefit of having more than one receiver on the sensor implant is that the recharging energy can be transmitted to different receivers at different times, an example of which was described above. Ultrasound beams transmitted to different receiving transducers (at different times) thus have a minimal amount or even no overlap (which can be controlled based on the position of the receiving transducers), which limits cumulative heating increases that can cause temperatures to rise quickly. Some devices that have a single receiving transducer, even if a catheter has more than one emitting transducer, can result in cumulative heating because the beams are always emitted towards the same receiving transducer and thus the tissue in that region is likely to overheat. There are thus, in general, significant benefits to having more than one receiving transducer (e.g., transducers 201) on the sensing implant, examples of which are set forth herein.

In any of the methods herein, after a transducer is deactivated (not transmitting energy), a temperature sensor can continue to sense temperature in the region near the deactivated transducer, and the catheter, with the use of an energy controller in operable communication with the transducers, can prevent the transducer from transmitting energy again until the temperature has returned to a desired temperature or the change in temperature is below a certain threshold again. So even if a second transducer has stopped transmitting, the first transducer might not resume transmitting energy immediately thereafter.

In some embodiments, the sensor implant comprises a plurality of piezoelectric receivers, and a single ultrasound transducer is carried by the catheter. In these embodiments, the path of the ultrasound beam emitted from the catheter may be steered (mechanically or via phasing) to be directed at a selected piezoelectric receiver, and the selected receivers may be alternated such that temperature rises are limited, including using any of concepts above. The system can be adapted to have automated catheter movement (e.g., automatically deflecting pullwires) to be able to automatically transmit to a desired receiver. In variations, the system may be adapted to stabilize the catheter to minimize movement and automate beam steering or focusing to automatically transmit to the desired receiver. In certain implementations, the distance between the distal tip of the catheter and the sensor implant will be sufficiently far such that near field overlap of ultrasound beams aimed at the various piezoelectric receivers is limited or removed, thus limiting the possibility of unwanted temperature rises in this overlap region.

In some alternative embodiments there may be an array of ultrasound transducers (in any configuration—e.g. 1×2, 2×2, 3×2, etc.) on the catheter and a corresponding array of piezoelectric receivers on the sensing implant, with spacing between adjacent transducers and between adjacent receivers such that when the catheter is maintained in a desired location, each transducer is located to selectively transmit towards one of the plurality of receivers. Depending on monitored tissue temperature at any one or more locations on or near the sensing implant, any combination of the transducers can be in active mode (transmitting energy), and any can be in standby or inactive mode (not transmitting). Any of the automated processes herein can be used to cease any of the transducers from transmitting at any time and can initiate the transmission of energy from any of the transducers at any time. When the catheter is in place and in use, some regions of tissue may heat up faster than others, and being able to selectively activate or selectively deactivate any transducer may be desirable to accelerate charge time and prevent overheating.

In some embodiments, the sensor implant may be implanted in an artery or in another lumen that experiences pulsatile or otherwise meaningful flow of a fluid or a gas. Such flow may cause the portions of the catheter body, such as the distal tip, to move due to the forces such flow exerts on the catheter apparatus. For example, when positioned in an artery, the tip of the catheter may be deflected periodically with each heart beat as the flow of blood accelerates through the vessel. These deflections may shift the relative positions of an acoustic receiver(s) on a sensor implant and a transmitting acoustic transducer(s) on the catheter, which limits charging efficiency and leads directly to unwanted tissue heating as portions of or the entirety of a transmitted acoustic beam are incident upon non-targeted locations.

To address this issue, in some embodiments, an acoustic-based recharging system may be adapted to utilize automated tracking of relevant locations on the sensor implant. For example, an ultrasound-based system may utilize adaptive focusing, beam steering, or transmission timing to keep the transmitted energy beam focused upon or otherwise incident upon the receiving transducer on the sensor. Some embodiments may utilize an ultrasound tracking system, for example using speckle-tracking or other related technologies known to those skilled in the art, to track the position of the receiver and automatically adjust the focusing, steering, or another property of the transmitted beam so that it remains aimed at the receiver. Due to the real-time capabilities of ultrasound tracking and associated refocusing/resteering, the system may be capable of maintaining a consistent or near-consistent aiming of the ultrasound beam upon the targeted area despite motion of the catheter, with little to no loss of transferred energy or other aiming-related inefficiencies. In some embodiments, a second ultrasound transducer (unrelated to the charging transducer) is located upon a portion of the catheter in a location proximate to the transducer utilized for charging. This secondary "aiming transducer" is configured to operate in a transmit/receive imaging mode, and captures ultrasound data in one or more spatial dimensions which can be processed and utilized to adjust the operation of the charging transducer. In alternative embodiments, the charging transducer may be adapted to operate in both charging and aiming modes, multiplexing between emitting charging pulses (e.g. high intensity, high duty cycle) used to transfer energy to the implanted sensor battery and emitting standard imaging pulses (e.g. low intensity, short duty cycle, high repetition rate) that can be utilized for tracking any relative position changes between the transmitting transducer and the acoustic receiver(s) on the sensor implant. This feature may be utilized instead of or in combination with any of the embodiments described herein or incorporated by reference herein, and may be adapted to include other features known to those skilled in the art that are not explicitly disclosed herein.

In any of the embodiments herein, temperature rises in overgrowth tissue may be, alternatively or in addition to any other process herein, limited by actively cooling the overgrowth region, the wall of the vessel proximate to the implant, or other relevant anatomic regions in the period before, during, or after recharging. In one implementation, a chilled circulating fluid can be actively pumped through a lumen in the recharging catheter to cool the surface of the catheter that interfaces with the overgrowth tissue covering the sensor implant. This pre-cooling technique will improve the resistance of the overgrowth tissue to problematic temperature rises. The cooling energy can alternatively or in addition to, be delivered to vessel walls nearby the implant to protect the vasculature, for example by releasing chilled saline into the bloodstream downstream from the recharging site (for example, out of a port on the catheter shaft). In these embodiments, the proximal end of the catheter would interface with one or more components that allows for providing a cooled fluid, examples of which are well-described in the art. Other ways of providing cooling, such as via expansion of a compressed gas, thermoelectric cooling, cooling via a phase-change material, and other methods known to those skilled in the art may be used in any of the embodiments herein.

Figure 3:
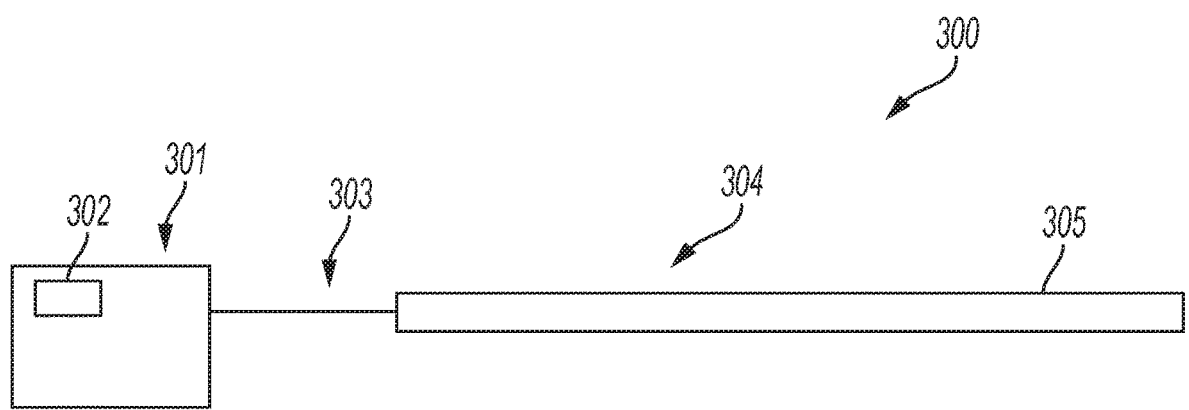
FIG. 3 illustrates an exemplary recharging catheter in communication with an external console.

FIG. 3 illustrates an exemplary recharging system 300 that includes a recharging catheter 304 that has a distal region 305 with one or more transducers, examples of which are shown in FIG. 2. Catheter 304 is in communication with external device 301 (e.g. an energy delivery console) via connection 303. External device 301 includes one or more energy controllers 302, which may have stored therein in one or more memory devices any number of algorithms adapted to execute any of the controller methods herein (e.g. controlling the start and/or stop of an electrical signal being delivered to the distal region 305 of the catheter 304).

Even if not specifically indicated, one or more methods or techniques described in this disclosure may be implemented, at least in part, in hardware, software, firmware or any combination thereof. For example, various aspects of the controller methods or controller components may he implemented within one or more processors, including one or more microprocessors, digital signal processors (DSPs), application specific integrated circuits (ASICs), field programmable gate arrays (FPGAs), programmable logic circuitry, or the like, either alone or in any suitable combination. The term "controller," "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure (e.g. controllers) may be embodied as instructions on a. computer-readable medium such as random access memory (RAM), read only memory (ROM), non-volatile RAM (NVRAM), electrically erasable programmable ROM (EEPROM), Flash memory, and the like. The instructions may be executed by a processor to support one or more aspects of the functionality described in this disclosure.

Any features of any devices, systems, or methods of use herein (including those incorporated by reference herein) can be combined with any other device, system or method herein (including those incorporated by reference herein) unless it is specifically indicated to the contrary.

The invention claimed is:

1. A catheter adapted for transmitting energy to an implantable sensing device, the catheter comprising:
   an energy transmission region in a distal region of the catheter, the energy transmission region including at least one transducer; and
   an expandable stabilization member in the distal region of the catheter, the stabilization member configured to be expanded semi-radially outward relative to a shaft of the catheter into an expanded configuration to:
   (a) come into contact with patient tissue and press and hold the distal region of the catheter against the implantable sensing device to stabilize the at least one transducer, and
   (b) form a lumen fully surrounded by the stabilization memberto permit flow of blood therethrough.

2. The catheter of claim 1, wherein the expandable stabilization member comprises an inflatable membrane.

3. The catheter of claim 1, wherein the expandable stabilization member is disposed on the catheter such that when expanded, the expandable stabilization member has a preferential direction of expansion relative to the catheter shaft, wherein the lumen is formed in the preferential direction of expansion relative to the catheter shaft.

4. The catheter of claim 3, wherein the preferential direction of expansion of the expandable stabilization member it allows the expandable stabilization member to expand solely to one side of the catheter shaft.

5. The catheter of claim 1, wherein the expandable stabilization member is disposed on the catheter such that when expanded, the expandable stabilization member and the shaft of the catheter are co-axial.

6. The catheter of claim 1, wherein the expandable stabilization member comprises at least one arm that is biased to expand semi-radially outward from a delivery configuration.

7. The catheter of claim 1 wherein the patient tissue is a blood vessel in which the catheter is positioned.

8. A method of stabilizing a recharging catheter, the method comprising:
   positioning an energy transmission region in a distal region of a recharging catheter adjacent a sensing implant in a body region through which blood is flowing, the sensing implant including a sensor, at least one receive transducer, and a rechargeable power source, the energy transmission region including at least one emit transducer;
   expanding a stabilization member semi-radially outward relative to a shaft of the recharging catheter into an expanded configuration, wherein expanding the stabilization membercomprises:
   (a) contacting patient tissue and pressing and holding the distal region of the recharging catheter against the sensing implant to stabilize the at least one emit transducer relative to the at least one receive transducer, and
   (b) forming a lumen fully surrounded by the stabilization member to permit flow of blood therethrough.

9. The method of claim 8, wherein expanding the stabilization member comprises inflating a balloon semi-radially outward.

10. The method of claim 8, wherein expanding the stabilization member semi-radially outward does not completely occlude the flow of blood in the body region.

11. The method of claim 8, wherein expanding the stabilization member semi-radially outward comprises expanding the stabilization member in a preferential expansion direction relative to the catheter shaft, wherein the lumen is formed in the preferential direction of expansion relative to the catheter shaft.

12. A catheter adapted for transmitting energy to an implantable sensing device, the catheter comprising:
   an energy transmission region in a distal region of the catheter, the energy transmission region including at least one transducer; and
   an expandable stabilization memberin the distal region of the catheter, the stabilization member configured to be expanded radially outward relative to a shaft of the catheter into an expanded configuration, wherein, when in the expanded configuration, the expandable stabilization member (i) has a preferential direction of expansion relative to the catheter shaft and (ii) forms a lumen on an inner portion of the expandable stabilization member, while a distal end of the catheter is pressed against the implantable sensing device maintaining contact with the patient tissue, wherein the lumen fully surrounded by the stabilization memberto permit flow of blood therethrough, wherein the lumen is formed in the preferential direction of expansion relative to the catheter shaft.

* * * * *